US010068116B2

(12) United States Patent
Good et al.

(10) Patent No.: US 10,068,116 B2
(45) Date of Patent: Sep. 4, 2018

(54) METHODS AND APPARATUS TO FACILITATE PROXIMITY DETECTION AND LOCATION TRACKING

(71) Applicant: General Electric Company, Schenectady, NY (US)

(72) Inventors: Brandon Stephen Good, Niskayuna, NY (US); Charles Burton Theurer, Alplaus, NY (US); Shaopeng Liu, Clifton Park, NY (US); Robert Lee Wallace, Glen Allen, VA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/407,873

(22) Filed: Jan. 17, 2017

(65) Prior Publication Data

US 2017/0124366 A1 May 4, 2017

Related U.S. Application Data

(63) Continuation of application No. 14/808,801, filed on Jul. 24, 2015, now Pat. No. 9,584,965.

(Continued)

(51) Int. Cl.
*G06Q 50/22* (2018.01)
*G06K 7/10* (2006.01)
(Continued)

(52) U.S. Cl.
CPC ........ *G06K 7/10425* (2013.01); *G01S 5/0289* (2013.01); *H04L 67/18* (2013.01); *H04W 4/028* (2013.01); *H04W 4/029* (2018.02)

(58) Field of Classification Search
CPC .... G06Q 50/22; G06Q 10/087; G06F 19/327; G06F 19/3406; G06F 19/3412; G01S 5/0284; G01S 5/0289
See application file for complete search history.

(56) References Cited

U.S. PATENT DOCUMENTS 6,344,794 B1   2/2002   Ulrich et al.
7,030,731 B2   4/2006   Lastinger et al.
(Continued)

FOREIGN PATENT DOCUMENTS

WO   0060374 A1      10/2000
WO   2015097314 A1   7/2015

OTHER PUBLICATIONS

United States Patent and Trademark Office, "Office Action," issued in connection with U.S. Appl. No. 14/808,624, dated Sep. 29, 2016, 9 pages.

(Continued)

*Primary Examiner* — Andrew Bee
(74) *Attorney, Agent, or Firm* — Hanley, Flight and Zimmerman, LLC

(57) ABSTRACT

Methods, apparatus, systems and articles of manufacture are disclosed to facilitate proximity detection and location tracking. An example method includes receiving messages collected by a badge in an environment, the messages including signal strength and a timestamp. The example method also includes assigning a location in the environment to the badge based on a first subset of the messages. The example method also includes identifying an asset in a second subset of the messages. The example method also includes updating a current location associated with the asset based on a relative proximity of the asset to the badge, wherein the current location corresponds to a first time and the updated location corresponds to a second time, and wherein a change in location between the current location and the updated location indicates movement of the asset in the environment.

20 Claims, 25 Drawing Sheets

Related U.S. Application Data

(60) Provisional application No. 62/029,252, filed on Jul. 25, 2014.

(51) Int. Cl.
*H04W 4/02* (2018.01)
*H04L 29/08* (2006.01)
*G01S 5/02* (2010.01)
*H04W 4/029* (2018.01)

(56) References Cited

U.S. PATENT DOCUMENTS

| | | | |
|---|---|---|---|
| 7,312,752 | B2 | 12/2007 | Smith |
| 7,586,413 | B2 | 9/2009 | Davis |
| 8,058,986 | B2 | 11/2011 | Klabunde et al. |
| 8,319,635 | B2 | 11/2012 | Perkins et al. |
| 8,368,540 | B2 | 2/2013 | Perkins et al. |
| 8,423,045 | B2 | 4/2013 | Parameswar |
| 8,457,656 | B2 | 6/2013 | Perkins et al. |
| 8,712,330 | B2 | 4/2014 | Desai et al. |
| 8,762,519 | B2 | 6/2014 | Thomson et al. |
| 8,847,754 | B2 | 9/2014 | Buchheim et al. |
| 8,948,782 | B2 | 2/2015 | Shang et al. |
| 9,031,577 | B2 | 5/2015 | Mirzaei et al. |
| 9,277,018 | B2 | 3/2016 | Kotecha et al. |
| 9,374,667 | B1 | 6/2016 | Jorgensen et al. |
| 2005/0035862 | A1 | 2/2005 | Wildman et al. |
| 2006/0261951 | A1 | 11/2006 | Koerner et al. |
| 2006/0290519 | A1* | 12/2006 | Boate ............... G07C 9/00111 340/573.4 |
| 2007/0241901 | A1 | 10/2007 | Cage et al. |
| 2010/0090901 | A1 | 4/2010 | Smith et al. |
| 2010/0188211 | A1 | 7/2010 | Brommer et al. |
| 2011/0050411 | A1 | 3/2011 | Schuman et al. |
| 2011/0080264 | A1 | 4/2011 | Clare et al. |
| 2012/0171960 | A1 | 7/2012 | Oshinsky et al. |
| 2013/0041623 | A1* | 2/2013 | Kumar ................ G01C 21/14 702/158 |
| 2014/0074667 | A1 | 3/2014 | Smith |
| 2014/0118113 | A1* | 5/2014 | Kaushik .............. H04W 12/12 340/8.1 |
| 2014/0180713 | A1 | 6/2014 | Tenarvitz et al. |
| 2014/0209676 | A1 | 7/2014 | Reynolds et al. |
| 2014/0327521 | A1* | 11/2014 | Chen ................ G06Q 10/087 340/8.1 |
| 2015/0105099 | A1 | 4/2015 | Luo et al. |
| 2015/0169916 | A1 | 6/2015 | Hill et al. |
| 2015/0382153 | A1 | 12/2015 | Otis et al. |
| 2016/0005300 | A1 | 1/2016 | Laufer et al. |
| 2016/0026837 | A1 | 1/2016 | Good et al. |
| 2016/0029160 | A1 | 1/2016 | Theurer et al. |
| 2017/0195852 | A1 | 7/2017 | Theurer et al. |

OTHER PUBLICATIONS

United States Patent and Trademark Office, "Notice of Allowance", issued in connection with U.S. Appl. No. 14/808,624, dated Dec. 21, 2016, 25 pages.

United States Patent and Trademark Office, "Notice of Allowance", issued in connection with U.S. Appl. No. 14/808,801, dated Oct. 17, 2016, 25 pages.

International Search Report and Written Opinion for International Application No. PCT/US2016/042946, dated Nov. 1, 2016. 11 pages.

United States Patent and Trademark Office, "Non-Final office action," issued in connection with U.S. Appl. No. 15/464,742, dated Jan. 12, 2018, 25 pages.

* cited by examiner

800

| Tag ID | Tag Type | Timestamp | RSSI | Channel Number |
|---|---|---|---|---|
| Entry_1 | Fixed-Location | 0:00:01 | High | 37 |
| Chair_1 | Mobile-Location | 0:00:02 | Low | 37 |
| Chair_1 | Mobile-Location | 0:00:03 | Med | 38 |
| ... | ... | ... | ... | ... |

Collected Beacon Messages

FIG. 8

Reader Messages Logged at the RTLS Server

| Reader ID | Tag ID | Tag Type | Timestamp | RSSI | Channel Number |
|---|---|---|---|---|---|
| Reader_1 | Entry_1 | Fixed-Location | 0:00:01 | High | 37 |
| Reader_1 | Chair_1 | Mobile-Location | 0:00:02 | Low | 37 |
| Reader_1 | Chair_1 | Mobile-Location | 0:00:03 | Med | 38 |
| ... | ... | ... | ... | ... | ... |

| Reader ID (1405) | Tag ID (1410) | Timestamp Interval (1415) | Reader Badge Location (1420) |
|---|---|---|---|
| Reader_1 | Entry 1 | 0:00:00 – 0:00:05 | Patient Room 1, Entry 1 |
| Reader_1 | Water Fountain 2 | 0:00:10 – 0:00:15 | Hallway 12, Water Fountain 2 |
| Reader_1 | Sink 2 | 0:02:20 – 0:02:25 | Patient Room 2, Sink 2 |
| ... | ... | ... | ... |

1450 → row 1, 1455 → row 2, 1460 → row 3

Reader Badge-Location Mappings

FIG. 14

| Tag ID | Current Location | Timestamp Interval | Asset-Location Confidence Score |
|---|---|---|---|
| Chair 2 | Patient Room 1, Entry 1 | 0:00:00 – 0:00:05 | 37 |
| Chair 3 | Hallway 2, Closet 3 | 0:00:00 – 0:00:05 | 1 |
| ... | ... | ... | ... |
| Walking Cane 12 | Patient Room 2, Sink 2 | 0:02:00 – 0:02:05 | 50 |
| Chair 2 | Hallway 12, Water Fountain 2 | 0:02:00 – 0:02:05 | 13 |
| ... | ... | ... | ... |

Mobile-Location Asset-Location Mappings and Corresponding Asset-Location Confidence Scores

FIG. 15

METHODS AND APPARATUS TO FACILITATE PROXIMITY DETECTION AND LOCATION TRACKING

RELATED APPLICATION

This patent arises from a continuation of U.S. patent application Ser. No. 14/808,801, filed on Jul. 24, 2015, entitled "Methods and Apparatus to Facilitate Proximity Detection and Location Tracking", which claims the benefit of U.S. Provisional Patent Application Ser. No. 62/029,252, filed Jul. 25, 2014, entitled "HOSPITAL TRACKING NETWORK." U.S. Non-Provisional patent application Ser. No. 14/808,801 and U.S. Provisional Patent Application Ser. No. 62/029,252 are hereby incorporated by reference herein in their entirety.

FIELD OF THE DISCLOSURE

This disclosure relates generally to healthcare environments, and, more particularly, to methods and apparatus to facilitate proximity detection and location tracking.

BACKGROUND

Industrial settings such as hospitals, construction sites, retail centers, etc. can be chaotic environments. A hospital is used herein as an example of an industrial setting. A hospital stay, for even straight-forward care, involves hundreds of healthcare resources. Healthcare resources include people (e.g., doctors, nurses, staff, etc.), processes and assets. The effectiveness of a healthcare system can be determined by the interaction between the healthcare resources. Adverse events that occur in hospitals, such as hospital-acquired infections, lost or missing assets, etc., result in patient harm, increased recovery time, loss of a hospital's and its staff's capacity to serve, unreimbursed healthcare costs, and, generally, increased healthcare costs. One of the main causes of these events is non-adherence to protocols. Protocols can refer to a series of preferred or prescribed tasks that (1) have been proven to reduce adverse events and (2) effect a desired elimination of activities, practices, or patterns that create harm or inefficiency. Example uses of such protocols are for hand washing, fall prevent, rounding, pain management, sleep improvement and physical therapy.

As an illustrative example, despite widespread knowledge that proper hand washing reduces pathogen transmission, adherence by visitors of patients under an infection control protocol and even hospital staff can remain low with mean baseline rates of routine compliance across organizations ranging from approximately 5%-81%, with an overall compliance of approximately 40%. While there are many reasons for non-compliance (including a perceived lack of risk, time to wash, missing knowledge of protocol, or associated discomfort from complying with protocol and general inconvenience) improvement in hand sanitization before coming in contact with patients and often upon completing contact, will reduce the spread of bacteria and thus lower the incidence of adverse events, thereby improving the standard of care. It is therefore advantageous to help the providers of healthcare and other persons involved in a patient's care or visitation to comply with protocols.

Real-time location systems (RTLS) monitor asset distribution and usage, providing actionable information to help control costs and improve the quality and efficiency of care. Systems that have been developed to track and analyze activities in clinical settings have included installing Radio Frequency Identification (RFID) or infrared (IR) reader infrastructures into buildings to capture position information. RFID sensors may be placed on the people and/or assets that need to be tracked.

In non-healthcare domains, such as commercial shopping monitoring, humans in effect become the sensors with such programs as "secret shoppers" and behavioral studies that use shopping patterns to infer consumer propensities to select product preferentially.

However, this is an expensive and time-consuming solution because it requires pulling power and data cabling to all the required locations. Location accuracy can also vary depending on technology. Typical RFID systems have a tolerance of approximately plus-or-minus ten feet, further limiting their range. RFID and IR-based sensors, though, are highly susceptible to drift due to interference in the environment (e.g., a patient room) and cross talk between locations that are physically separated, but have a line of sight between them (e.g., two patient rooms across the hall from each other).

Therefore, it would be desirable to design a system and method for tracking locations and interactions between people and assets in an environment with minimal infrastructure requirements and standardized technologies.

BRIEF DESCRIPTION

Certain examples provide a method to facilitate proximity detection and location tracking in an environment. The example method includes receiving messages collected by a badge in the environment, the messages including signal strength and a timestamp. The example method includes assigning a location in the environment to the badge based on a first subset of the messages. The example method also includes identifying an asset in a second subset of the messages, and updating a current location associated with the asset based on a relative proximity of the asset to the badge, wherein the current location corresponds to a first time and the updated location corresponds to a second time, and wherein a change in location between the current location and the updated location indicates movement of the asset in the environment.

Another example includes an apparatus to facilitate proximity detection and location tracking in an environment. The example apparatus includes a message receiver to receive messages collected by a badge in the environment, the received messages to include signal strength and a timestamp. The example apparatus also includes a badge location engine to assign a location in the environment to the badge based on a first subset of the messages that correspond to a timestamp interval. The example apparatus also includes an asset location engine to identify an asset in a second subset of the messages that correspond to mobile-location assets, and to update a current location associated with the asset based on a relative proximity of the asset to the badge, the current location to correspond to a first time and the updated location to correspond to a second time, and a change in location between the current location and the current location indicative of movement of the asset in the environment.

Another example includes a tangible machine-readable storage medium comprising instructions that, when executed, cause a machine to at least receive messages collected by a badge in an environment, the received messages to include signal strength and a timestamp. The example instructions to also cause the machine to assign a location in the environment to the badge based on a first subset of the messages that correspond to a timestamp interval by identifying a proximate beacon tag relative to the badge based on the signal strength, and assign a fixed-location associated with the proximate beacon tag to the badge. The example instructions to also cause the machine to identify an asset in a second subset of the messages that correspond to mobile-location assets. The example instructions to also cause the machine to update a current location associated with the asset based on a relative proximity of the asset to the badge by classifying an asset location relative to the badge based on the signal strength. The example instructions to cause the machine to, in response to classifying the asset location as immediate relative to the badge, associate the location assigned to the badge to the asset, and increment a confidence score associated with the asset. The example instructions to cause the machine to, in response to classifying the asset location as near relative to the badge, increment the confidence score associated with the asset when the current location associated with the asset matches the location of the badge, and decrement the confidence score associated with the asset location when the current location associated with the asset is different from the location of the badge, wherein the current location is to correspond to a first time and the updated location is to correspond to a second time, and a change in location between the current location and the updated location is to indicate movement of the asset in the environment.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

FIG. 8 illustrates an example data table that may be employed by the example reader badge of FIG. 4 to store collected beacon messages.

FIG. 13 illustrates an example data table that may be employed by the example RTLS server of FIG. 4 to record received reader messages.

FIG. 14 illustrates an example data table that may be employed by the example RTLS server of FIG. 4 to store reader badge-location mappings.

FIG. 15 illustrates an example data table that may be employed by the example RTLS server of FIG. 4 to store mobile-location asset-location mappings and corresponding asset-location confidence scores.

DETAILED DESCRIPTION

Figure 1:
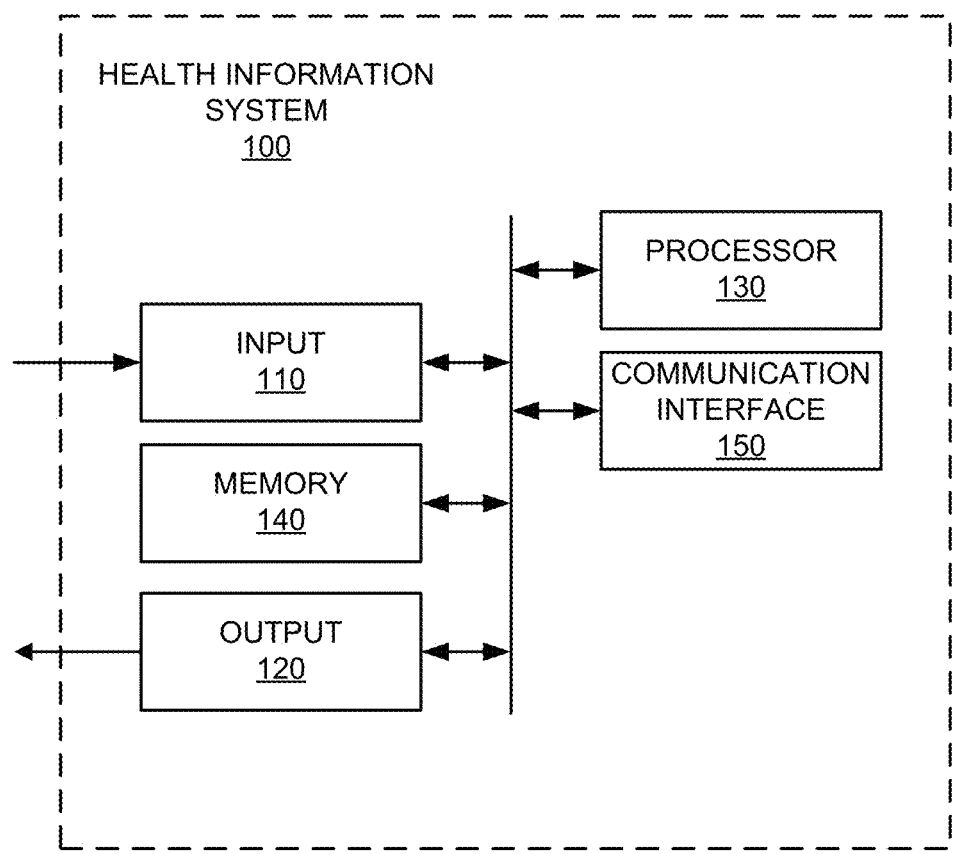
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Certain examples of the presently disclosed technology improve proximity detection and location tracking of resources in an environment such as a hospital. An example system disclosed herein includes one or more beacon tags affixed to assets within the environment and that transmit (e.g., periodically, aperiodically and/or as a one-time event) beacon messages. The beacon messages are received by a mobile reader badge that listens for beacon messages transmitted in the environment. For example, disclosed example reader badges (sometimes referred to herein as "readers," "badges" or "mobile wireless bridges") may include a network interface to receive beacon messages transmitted via low power Bluetooth Low Energy (BLE). In some disclosed examples, the reader badges process the received beacon messages and communicate information obtained from the beacon messages to one or more real-time location services (RTLS) servers via a communication infrastructure. For example, disclosed example reader badges may aggregate and communicate a batch of beacon messages (e.g., a threshold number of beacon messages, a threshold interval of time (e.g., a window of interest), etc.) to an RTLS server via a Wi-Fi infrastructure (e.g., a wireless network). In some disclosed examples, the RTLS server processes the received batch of beacon messages to facilitate real-time location tracking of the resources in the environment. In some disclosed examples, the RTLS server may report the location of resources via charts, graphs, tables, etc.

Real-time location services enable improved patient workflow via proximity detection and location tracking in a healthcare environment, such as a hospital. Location tracking can be used to locate resources such as mobile assets (e.g., patients, intravenous (IV) pumps, telemetry units, wheelchairs, etc.) within the hospital. For example, location tracking can be used to locate a "lost" or "missing" IV pump within a patient's room. Proximity detection facilitates an improved understanding of how interactions occur during the patient workflow. For example, based on the proximity to a soap dispenser, a user (e.g., a system administrator) can determine whether a caretaker washed their hands prior to interacting with a patient.

Examples systems and methods disclosed herein facilitate improved proximity detection and location tracking by creating a hospital tracking network within the hospital using the communication infrastructure already installed in the hospital. Beacon tags are installed throughout a location or building. For example, beacon tags can be affixed to stationary assets (e.g., patient room entry ways, sinks, water fountains, hallways, etc.) and mobile assets such as hospital beds, IV pumps, soap dispensers, etc. In some disclosed examples, the beacon tags are also included in disposable patient tags provided to the patient upon admission of a hospital stay. Beacon tags are low-cost, low-power transmitters of beacon messages. A beacon message (sometimes referred to herein as a "beacon") includes information about the beacon tag such as a unique identifier (e.g., a tag identifier such as a media access control (MAC) address) and a tag type identifier (e.g., whether the beacon tag is affixed to a fixed-location asset or to a mobile asset). In some disclosed examples, the beacon tags broadcast (e.g., advertise, communicate, transmit, etc.) beacon messages at pre-set frequencies (e.g., ten times a second, once a second, once a minute, etc.). For example, a beacon tag affixed to a fixed-location asset (e.g., a sink) may broadcast beacon messages ten times a second, while a beacon tag affixed to a mobile asset (e.g., a wheelchair) may broadcast beacon messages at relatively shorter intervals (e.g., once a second).

A reader badge is a mobile wireless bridge that facilitates mobile tracking by "listening" and receiving beacon messages broadcast by beacon tags. The reader badge includes a BLE controller to receive connection-less beacon messages broadcast by beacon tags. The reader badge also includes a Wi-Fi controller to establish a connection with an RTLS server. The reader badge may be worn or transported by hospital caregivers. For example, a reader badge may be worn as a lanyard or clipped to the caregiver's clothing. As the caregiver moves about the hospital, the reader badge passively collects beacon messages and communicates reader messages to an RTLS server at the backend of the system. In some examples, the reader badge collects a number (e.g., a predetermined number) of beacon messages or waits a period (e.g., a predetermined period of time) prior to communicating the reader messages. In some examples, the reader badge generates and communicates a reader message as a beacon message from a beacon tag is received. A reader message includes information received from the beacon message such as a unique identifier of the source beacon tag and a spatial location of the source beacon tag. In some examples, the reader badge includes a timestamp identifying when the beacon message was received by the reader badge in the reader message. In some examples, the reader badge includes a received signal strength indication (RSSI) value (e.g., a power ratio in decibels of the measured power to one milli-watt (dBm)).

Example reader badges disclosed herein include a proximity engine to process the beacon messages and determine distance from the source (e.g., the beacon tag that broadcast the corresponding beacon message). For example, a hospital room may include a first beacon tag affixed to a door, a second beacon tag affixed to an infusion pump, a third beacon tag affixed to a bed, and a fourth beacon tag included in a patient tag (e.g., a disposable bracelet including patient identification information such as name, sex, date of birth information). As the caregiver moves about the hospital room, the reader badge may receive beacon messages from each of the beacon tags. The proximity engine can determine the RSSI strength for each of the beacon messages and associate RSSI strength with a respective beacon tag.

In some examples, the proximity engine determines which beacon tags are proximate (e.g., near or closely located) to the reader badge. For example, the proximity engine can compare the RSSI strength of a beacon message to a threshold and if the RSSI strength satisfies the threshold (e.g., the RSSI strength is greater than a threshold), the proximity engine identifies the source beacon tag as proximate to the reader badge. In some examples, the proximity engine discards beacon messages that are not proximate to the reader badge.

Example systems and methods disclosed herein include an RTLS server that monitors and/or reports tracking location and interactions between people and assets in an environment. For example, the RTLS server can aggregate reader messages from the one or more reader badges included in an environment (e.g., the hospital). The RTLS server may be in connection with the reader badges via a wireless Intranet network (e.g., a wireless local area network, etc.) and/or a wireless Internet connection.

II. Example Operating Environment

Health information, also referred to as healthcare information and/or healthcare data, relates to information generated and/or used by a healthcare entity. Health information can include reader messages and RTLS server information, for example. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) purpose and an administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data models (CDM) and common service models (CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. The example healthcare-focused information system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), RTLS server, and/or other health information system (e.g., clinical information system (CIS), hospital information system (HIS), patient data management system (PDMS), laboratory information system (LIS), cardiovascular information system (CVIS), etc.

As illustrated in FIG. 1, the example healthcare-focused information system 100 includes an input 110, an output 120, a processor 130, a memory 140, and a communication interface 150. The components of the example healthcare-focused information system 100 can be integrated in one device or distributed over two or more devices.

The example input 110 of FIG. 1 may include a keyboard, a touch-screen, a mouse, a trackball, a track pad, optical barcode recognition, voice command, etc. or combination thereof used to communicate an instruction or data to the example healthcare-focused information system 100. The example input 110 may include an interface between systems, between user(s) and the healthcare-focused information system 100, etc.

The example output 120 of FIG. 1 can provide a display generated by the processor 130 for visual illustration on a monitor or the like. The display can be in the form of a network interface or graphic user interface (GUI) to exchange data, instructions, or illustrations on a computing device via the communication interface 150, for example. The example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

The example processor 130 of FIG. 1 includes hardware and/or software configuring the hardware to execute one or more tasks and/or implement a particular system configuration. The example processor 130 processes data received at the input 110 and generates a result that can be provided to one or more of the output 120, the memory 140, and the communication interface 150. For example, the example processor 130 can take user annotation provided via the input 110 with respect to an image displayed via the output 120 and can generate a report associated with the image based on the annotation. As another example, the example processor 130 can process updated patient information obtained via the input 110 to provide an updated patient record to an EMR via the communication interface 150.

The example memory 140 of FIG. 1 may include a relational database, an object-oriented database, a data dictionary, a clinical data repository, a data warehouse, a data mart, a vendor neutral archive, an enterprise archive, etc. The example memory 140 stores images, patient data, best practices, clinical knowledge, analytics, reports, etc. The example memory 140 can store data and/or instructions for access by the processor 130. In certain examples, the memory 140 can be accessible by an external system via the communication interface 150.

In certain examples, the memory 140 stores and controls access to encrypted information, such as patient records, encrypted update-transactions for patient medical records, including usage history, etc. In an example, medical records can be stored without using logic structures specific to medical records. In such a manner, the memory 140 is not searchable. For example, a patient's data can be encrypted with a unique patient-owned key at the source of the data. The data is then uploaded to the memory 140. The memory 140 does not process or store unencrypted data thus minimizing privacy concerns. The patient's data can be downloaded and decrypted locally with the encryption key.

For example, the memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories.

Document information may include an identifier, a patient identifier, a clinic identifier, a security category, and encrypted data, for example.

The example communication interface 150 of FIG. 1 facilitates transmission of electronic data within and/or among one or more systems. Communication via the communication interface 150 can be implemented using one or more protocols. In some examples, communication via the communication interface 150 occurs according to one or more standards (e.g., Digital Imaging and Communications in Medicine (DICOM), Health Level Seven (HL7), ANSI X12N, etc.). The example communication interface 150 can be a wired interface (e.g., a data bus, a Universal Serial Bus (USB) connection, etc.) and/or a wireless interface (e.g., radio frequency, infrared, near field communication (NFC), etc.). For example, the communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
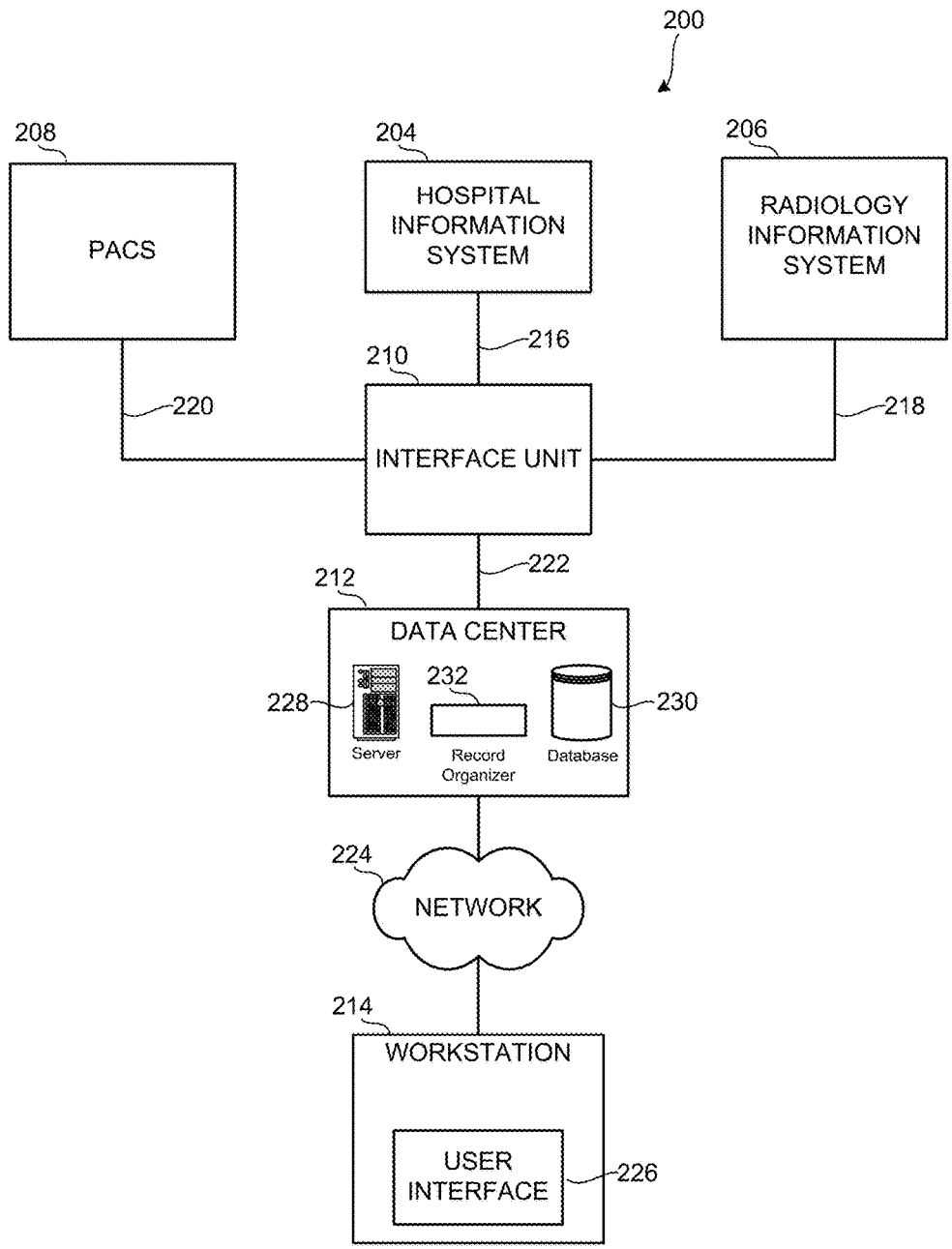
FIG. 2 shows a block diagram of an example healthcare information infrastructure including one or more systems.

FIG. 2 shows a block diagram of an example healthcare information system (e.g., an infrastructure) 200 including one or more subsystems such as the example healthcare-related information system 100 illustrated in FIG. 1. The example healthcare information system 200 of FIG. 2 includes a HIS 204, a RIS 206, a PACS 208, an interface unit 210, a data center 212, and a workstation 214. In the illustrated example, the HIS 204, the RIS 206, and the PACS 208 are housed in a healthcare facility and locally archived. However, in other implementations, the HIS 204, the RIS 206, and/or the PACS 208 may be housed within one or more other suitable locations. In certain implementations, one or more of the HIS 204, the RIS 206, the PACS 208, etc., may be implemented remotely via a thin client and/or downloadable software solution. Furthermore, one or more components of the healthcare information system 200 can be combined and/or implemented together. For example, the RIS 206 and/or the PACS 208 can be integrated with the HIS 204, the PACS 208 can be integrated with the RIS 206, and/or the three example information systems 204, 206, and/or 208 can be integrated together. In other example implementations, the healthcare information system 200 includes a subset of the illustrated information systems 204, 206, and/or 208. For example, the healthcare information system 200 may include only one or two of the HIS 204, the RIS 206, and/or the PACS 208. Information (e.g., scheduling, test results, exam image data, observations, diagnosis, etc.) can be entered into the HIS 204, the RIS 206, and/or the PACS 208 by healthcare practitioners (e.g., radiologists, physicians, and/or technicians) and/or administrators before and/or after patient examination. One or more of the HIS 204, the RIS 206, and/or the PACS 208 can include and/or communicate with an RTLS server and can communicate with equipment and system(s) in an operating room, patient room, etc., to track activity, correlate information, generate reports and/or next actions, and the like.

In the illustrated example of FIG. 2, the HIS 204 stores medical information such as clinical reports, patient information, and/or administrative information received from, for example, personnel at a hospital, clinic, and/or a physician's office (e.g., an EMR, EHR, PHR, etc.). The example RIS 206 of the illustrated example of FIG. 2 stores information such as, for example, radiology reports, radiology exam image data, messages, warnings, alerts, patient scheduling information, patient demographic data, patient tracking information, and/or physician and patient status monitors. Additionally, the RIS 206 enables exam order entry (e.g., ordering an x-ray of a patient) and image and film tracking (e.g., tracking identities of one or more people that have checked out a film). In some examples, information in the RIS 206 is formatted according to the HL-7 (Health Level Seven) clinical communication protocol. In certain examples, a medical exam distributor is located in the RIS 206 to facilitate distribution of radiology exams to a radiologist workload for review and management of the exam distribution by, for example, an administrator.

In the illustrated example of FIG. 2, the PACS 208 stores medical images (e.g., x-rays, scans, three-dimensional renderings, etc.) as, for example, digital images in a database or registry. In some examples, the medical images are stored in the PACS 208 using the Digital Imaging and Communications in Medicine (DICOM) format. Images are stored in the PACS 208 by healthcare practitioners (e.g., imaging technicians, physicians, radiologists) after a medical imaging of a patient and/or are automatically transmitted from medical imaging devices to the PACS 208 for storage. In some examples, the PACS 208 can also include a display device and/or viewing workstation to enable a healthcare practitioner or provider to communicate with the PACS 208.

In the illustrated example of FIG. 2, the interface unit 210 includes a HIS interface connection 216, a RIS interface connection 218, a PACS interface connection 220, and a data center interface connection 222. The example interface unit 210 facilities communication among the HIS 204, the RIS 206, the PACS 208, and/or data center 212. In the illustrated example, the interface connections 216, 218, 220, 222 are implemented by a Wide Area Network (WAN) such as a private network or the Internet. Accordingly, the interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with the workstation 214, via a network 224, implemented at a plurality of locations (e.g., a hospital, clinic, doctor's office, other medical office, or terminal, etc.). The network 224 is implemented by, for example, the Internet, an intranet, a private network, a wired or wireless Local Area Network, and/or a wired or wireless Wide Area Network. In some examples, the interface unit 210 also includes a broker (e.g., a Mitra Imaging's PACS Broker) to allow medical information and medical images to be transmitted together and stored together.

In the illustrated example, the interface unit 210 receives images, medical reports, administrative information, exam workload distribution information, and/or other clinical information from the information systems 204, 206, 208 via the corresponding interface connections 216, 218, 220. If necessary (e.g., when different formats of the received information are incompatible), the interface unit 210 translates or reformats (e.g., into Structured Query Language ("SQL") or standard text) the medical information, such as medical reports, to be properly stored at the data center 212. The reformatted medical information can be transmitted using a transmission protocol to enable different medical information to share common identification elements, such as a patient name or social security number. Next, the interface unit 210 transmits the medical information to the data center 212 via the data center interface connection 222. Finally, medical information is stored in the data center 212 in, for example, the DICOM format, which enables medical images and corresponding medical information to be transmitted and stored together.

The medical information is later viewable and easily retrievable at the workstation 214 (e.g., by their common identification element, such as a patient name or record number). The workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The example workstation 214 of FIG. 2 receives commands and/or other input from a user via, for example, a keyboard, mouse, track ball, microphone, etc. The workstation 214 is capable of implementing a user interface 226 to enable a healthcare practitioner and/or administrator to interact with the healthcare information system 200. For example, in response to a request from a physician, the user interface 226 presents a patient medical history. In other examples, a radiologist is able to retrieve and manage a workload of exams distributed for review to the radiologist via the user interface 226. In further examples, an administrator reviews radiologist workloads, exam allocation, and/or operational statistics associated with the distribution of exams via the user interface 226. In some examples, the administrator adjusts one or more settings or outcomes via the user interface 226.

The example data center 212 of FIG. 2 is an archive to store information such as images, data, medical reports, and/or, more generally, patient medical records. In addition, the data center 212 can also serve as a central conduit to information located at other sources such as, for example, local archives, hospital information systems/radiology information systems (e.g., the HIS 204 and/or the RIS 206), or medical imaging/storage systems (e.g., the PACS 208 and/or connected imaging modalities). That is, the data center 212 can store links or indicators (e.g., identification numbers, patient names, or record numbers) to information. In the illustrated example, the data center 212 is managed by an application server provider (ASP) and is located in a centralized location that can be accessed by a plurality of systems and facilities (e.g., hospitals, clinics, doctor's offices, other medical offices, and/or terminals). In some examples, the data center 212 can be spatially distant from the HIS 204, the RIS 206, and/or the PACS 208.

In the illustrated example, the example data center 212 of FIG. 2 includes a server 228, a database 230, and a record organizer 232. The server 228 receives, processes, and conveys information to and from the components of the healthcare information system 200. The database 230 stores the medical information described herein and provides access thereto. The example record organizer 232 of FIG. 2 manages patient medical histories, for example. The record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by the healthcare information system 200 via a software-as-a-service (SaaS) implementation over a cloud or other computer network, for example. In certain examples, all or part of the healthcare information system 200 can also be provided via platform as a service (PaaS), infrastructure as a service (IaaS), etc. For example, the healthcare information system 200 can be implemented as a cloud-delivered Mobile Computing Integration Platform as a Service. A set of consumer-facing Web-based, mobile, and/or other applications enable users to interact with the PaaS, for example.

C. Industrial Internet Examples

The Internet of things (also referred to as the "Industrial Internet") relates to an interconnection between a device that can use an Internet connection to talk (e.g., communicate) with other devices on the network. Using the connection, devices can communicate to trigger events/actions (e.g., changing temperature, turning on/off, providing a status, etc.). In certain examples, machines can be merged with "big data" to improve efficiency and operations, providing improved data mining, facilitate better operation, etc.

Big data can refer to a collection of data so large and complex that it becomes difficult to process using traditional data processing tools/methods. Challenges associated with a large data set include data capture, sorting, storage, search, transfer, analysis, and visualization. A trend toward larger data sets is due at least in part to additional information derivable from analysis of a single large set of data, rather than analysis of a plurality of separate, smaller data sets. By analyzing a single large data set, correlations can be found in the data, and data quality can be evaluated.

Figure 3:
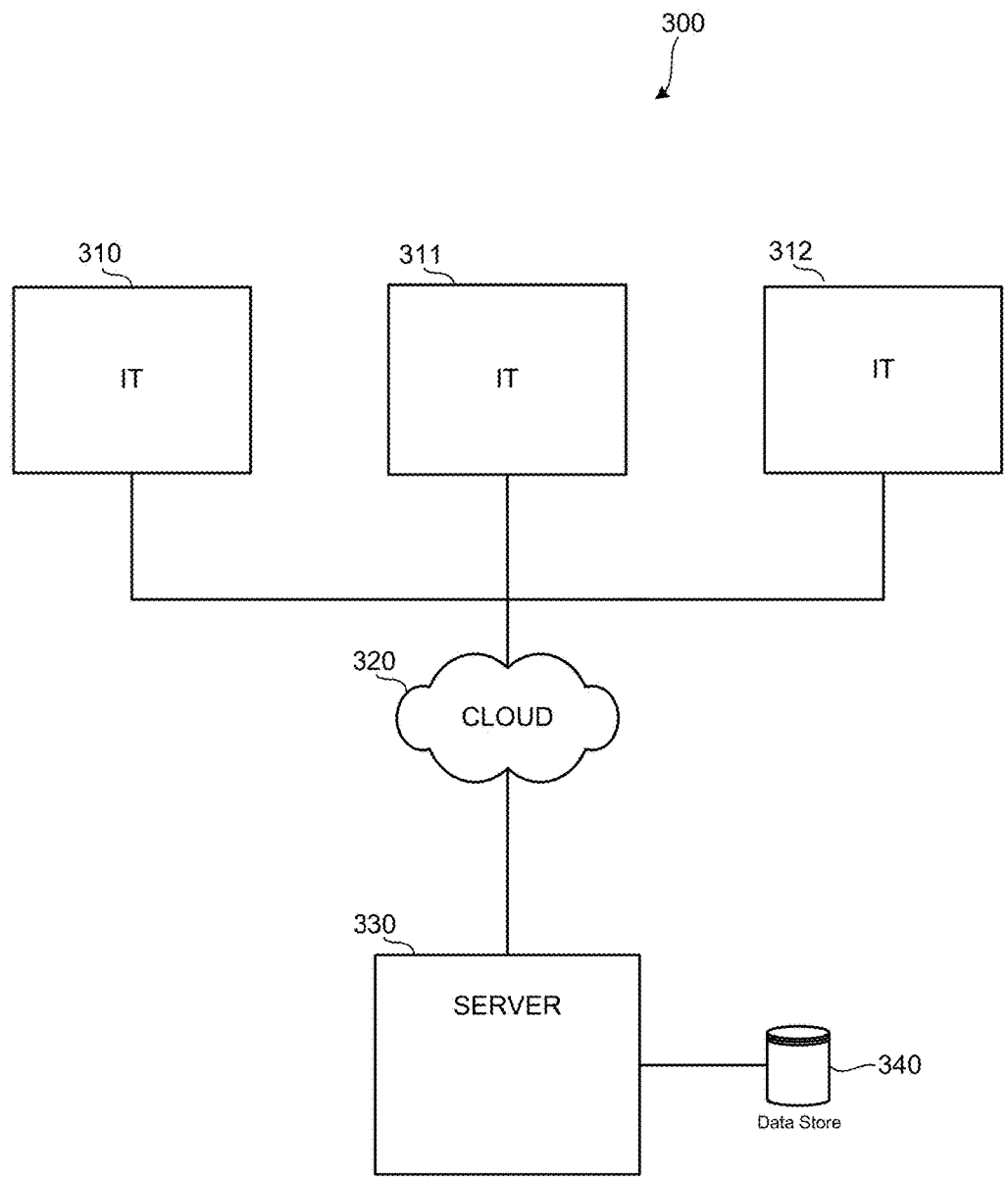
FIG. 3 shows an example industrial internet configuration including a plurality of health-focused systems.

FIG. 3 illustrates an example industrial internet configuration 300. The example industrial internet configuration 300 includes a plurality of health-related assets 310-312 (sometimes referred to herein as health-focused systems or infrastructures) (e.g., information systems, imaging modalities, etc.), such as a plurality of health information systems 100 (e.g., PACS, RIS, EMR, etc.) communicating via the industrial internet configuration 300. The example industrial internet configuration 300 of FIG. 3 includes a plurality of health-related assets 310-312 communicating with a server 330 and an associated data store 340 via a cloud 320.

As shown in the example of FIG. 3, a plurality of health-related assets 310-312 can access the cloud 320, which connects the assets 310-312 with the server 330 and the associated data store 340. Information systems, for example, include communication interfaces to exchange information with the server 330 and the data store 340 via the cloud 320. Other assets, such as medical imaging scanners, patient monitors, etc., can be outfitted with sensors and communication interfaces to enable them to communicate with each other and with the server 330 via the cloud 320.

Thus, the example health-related assets 310-312 within the industrial internet configuration 300 become "intelligent" as a network with advanced sensors, controls, analytical-based decision support and hosting software applications. Using such an infrastructure, advanced analytics can be provided to associated data. The analytics combines physics-based analytics, predictive algorithms, automation, and deep domain expertise. Via the example cloud 320, the health-related assets 310-312 and associated people can be connected to support more intelligent design, operations, maintenance, and higher server quality and safety, for example.

Using the industrial internet infrastructure, for example, a proprietary machine data stream can be extracted from the asset 310. Machine-based algorithms and data analysis are applied to the extracted data. Data visualization can be remote, centralized, etc. Data is then shared with authorized users, and any gathered and/or gleaned intelligence is fed back into the assets 310-312.

D. Data Mining Examples

Imaging informatics includes determining how to tag and index a large amount of data acquired in diagnostic imaging in a logical, structured, and machine-readable format. By structuring data logically, information can be discovered and utilized by algorithms that represent clinical pathways and decision support systems. Data mining can be used to help ensure patient safety, reduce disparity in treatment, provide clinical decision support, etc. Mining both structured and unstructured data from radiology reports, as well as actual image pixel data, can be used to tag and index both imaging reports and the associated images themselves.

E. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In some examples, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle management, population health management, patient identity, consent management, etc.

III. Example Hospital Tracking Network

Real-time location services (RTLS) facilitate tracking people and assets in an industrial setting, such as a hospital. The example RTLS system described herein is designed to create location awareness of assets by capturing location and proximity information from beacon tags installed throughout the hospital. Examples disclosed herein utilize reader badges worn by healthcare workers (e.g., doctors, nurses, administrators, janitors, etc.) that receive beacon messages from beacon tags that are installed in and/or affixed to assets such as hallways, rooms, equipment, patients, etc. for which location and/or proximity information is to be collected between the beacon tags and the tagged asset. For example, the beacon tags may broadcast beacon messages including a unique identifier (e.g., a signature, a MAC address, a serial number, etc.) associated with the corresponding beacon tags. As the healthcare workers walk around the hospital, their reader badges collect beacon messages transmitted from beacon tags throughout the hospital. In some disclosed examples, the reader badges aggregate the beacon messages and transmit a batch of beacon messages to an RTLS server for processing. The example RTLS server disclosed herein processes the beacon messages to create location awareness through proximity and probability.

In some disclosed examples, beacon tags are installed in and/or attached to fixed-location (e.g., placed on stationary (or near stationary)) assets. For example, some "known location" beacon tags may be affixed to hallways, doors, windows, sinks, etc. As disclosed below, in some examples, the RTLS server utilizes the beacon messages received from "known location" beacon tags to determine a location for the reader badge.

In some disclosed examples, beacon tags are affixed to mobile assets such as equipment. For example, some "mobile location" beacon tags may be affixed to beds, wheelchairs, patients, etc. As disclosed below, in some examples, the RTLS server utilizes the beacon messages received from the "mobile location" beacon tags to determine what assets are near the corresponding reader badges (e.g., the reader badge that aggregated and transmitted a batch of beacon messages).

In addition, comparing the asset locations during different timestamp intervals may be useful in determining how the assets were moved and/or when caregivers interacted with the assets. For example, consider an example in which a wheelchair (e.g., a mobile-location asset) is located in a first patient room. In the illustrated example, assume that the wheelchair is affixed with a mobile-location asset beacon tag and that the first patient room is affixed with a fixed-location asset beacon tag. In the illustrated example, when a caregiver wearing a reader badge walks into the first patient room, their reader badge collects beacon messages broadcast by the wheelchair beacon tag and the first patient room beacon tag. In the illustrated example, the caregiver location is assigned to the first patient room based on the beacon messages broadcast by the first patient room beacon tag. In addition, since the wheelchair is "seen" in the same location, the wheelchair location may also be updated to the first patient room.

In the illustrated example, while the caregiver is in the first patient room, their reader badge collects beacon messages broadcast by the wheelchair beacon tag and the first patient room beacon tag. If the caregiver begins moving the wheelchair (e.g., from the first patient room to a second patient room), their reader badge will continue to collect beacon tags broadcast by the first patient room badge tag, but will also begin collecting beacon messages broadcast by a second patient room beacon tag. In the illustrated example, once the caregiver enters the second patient room, the caregiver location is updated to the second patient room. Additionally, in the illustrated example, since the wheelchair is still "seen" by the caregiver (e.g., the wheelchair location is determined to be proximate to the caregiver), the location of the wheelchair is also updated to the second patient room.

In the illustrated example, after the wheelchair is moved from the first patient room to the second patient room, confidence that the wheelchair is located in the second patient room rather than the first patient room may be low. However, in the illustrated example, each time a caregiver walks into the first patient room and does not "see" the wheelchair, confidence that the wheelchair is located in the first patient room decreases. Additionally, in the illustrated example, each time a caregiver walks into the second patient room and does "see" the wheelchair, confidence that the wheelchair is located in the second patient room increases. In the illustrated example, the "crowd" (e.g., the caregivers) provides different snapshots of what is "seen" at different locations and at different times. As disclosed herein, an RTLS server may analyze the different snapshots to facilitate proximity detection and location tracking of assets in an environment.

Figure 4:
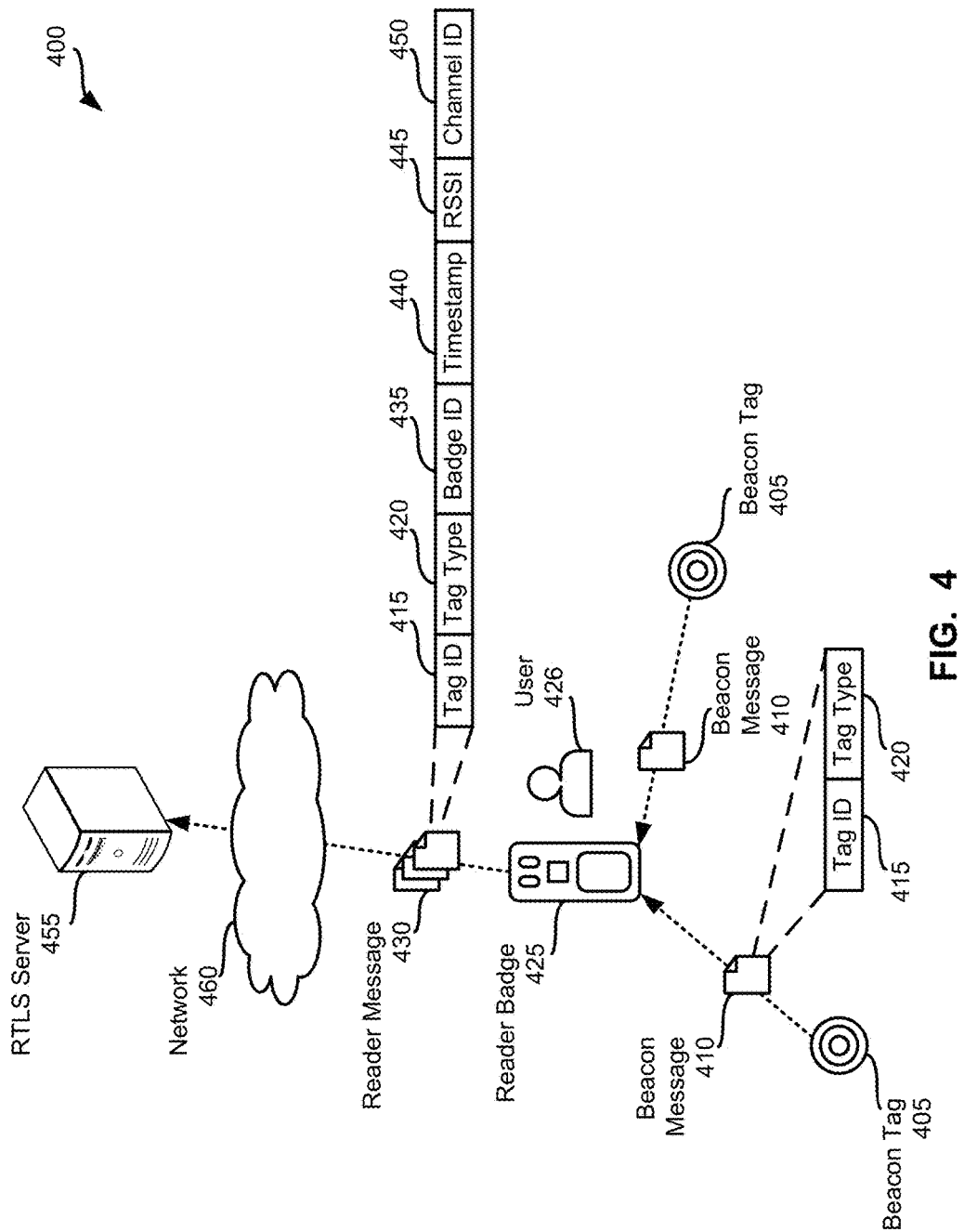
FIG. 4 is a block diagram illustrating an example environment constructed in accordance with the teachings of this disclosure to facilitate proximity detection and location tracking.

Referring to FIG. 4, an example environment 400 in which examples disclosed herein may be implemented to facilitate proximity detection and location tracking using a mobile wireless bridge is illustrated. The example environment 400 of FIG. 4 includes example beacon tags 405, an example reader badge 425 and an example real-time locations services (RTLS) server 455.

In the illustrated example of FIG. 4, the beacon tags 405 are implemented using low-power BLE transmitters and include a single coin-cell battery. In some examples, the single coin-cell battery provides power to the corresponding beacon tag 405 for two or more years. In the illustrated example, beacon tags 405 are installed throughout the environment 400 on two types of assets. For example, one or more beacon tag(s) 405 may be located on (e.g., affixed to) fixed-location assets such as doors, rooms, hallways, water fountains, etc. In addition, one or more beacon tag(s) 405 may be located on (e.g., affixed to) mobile-location assets such as patients (e.g., inserted within a patient tag), beds, IV pumps, wheelchairs, etc. Although the illustrated example of FIG. 4 includes only two beacon tags 405, other environments are likely to include additional beacon tags. For example, different environments may include tens, hundreds and/or thousands of beacon tags affixed to assets. In general, accuracy of the proximity detection and location tracking of assets in an environment is increased and/or decreased based on adding or reducing the number of beacon tags placed in the environment.

In the illustrated example of FIG. 4, the example beacon tags 405 periodically advertise their presence in the environment 400. For example, the beacon tags 405 may broadcast example beacon messages 410 every one second. In other examples, the beacon tags 405 may broadcast beacon messages 410 aperiodically and/or as a one-time event. In some examples, the beacon tags 405 may broadcast beacon messages 410 at different time intervals. For example, beacon tags 405 located on fixed-location assets may broadcast beacon messages 410 every two seconds, while beacon tags 405 located on mobile-location assets may broadcast beacon messages 410 every second. In some examples, beacon tags located on mobile-locations assets may broadcast beacon messages 410 at a first frequency (e.g., once every second) while the mobile-location asset is stationary and may broadcast beacon messages 410 at a second frequency (e.g., once every half-second) while the mobile-location asset is moving. However, other time intervals may additionally or alternatively be used.

In the illustrated example, the beacon messages 410 include tag identifying information 415 and tag-type identifying information 420. For example, tag identifying information 415 may be a unique identifier of the beacon tag 405 such as a MAC address, a serial number, an alphanumeric signature, etc. The example tag-type identifying information 420 identifies whether the beacon tag 405 broadcasting the beacon message 410 is affixed to a fixed-location asset or affixed to a mobile-location asset. However, the beacon messages 410 may include additional or alternative information. For example, the beacon messages 410 may include information identifying the software version being executed by the beacon tags 405, may include information identifying a power level of the beacon tag 405, etc.

In the illustrated example of FIG. 4, the beacon messages 410 are received by the reader badge 425. In the illustrated example, the reader badge 425 is worn by a hospital caregiver 426 such as a doctor, a nurse, etc. As the hospital caregiver moves through the hospital, the reader badge 425 collects beacon messages 410 broadcast by the beacon tags 405. For example, while the hospital worker 426 is visiting a patient in an example patient room #1, the example reader badge 410 may collect one or more beacon message(s) from a fixed-location asset beacon tag located on a door of the patient room #1, one or more beacon message(s) from a fixed-location asset beacon tag located on a sink in the patient room #1, one or more beacon message(s) from a mobile-location asset beacon tag located on the patient's identification tag, one or more beacon message(s) from a mobile-location asset beacon tag located on a bed in the patient room #1, etc.

In the illustrated example of FIG. 4, the reader badge 425 generates example reader messages 430 in response to receiving the beacon messages 410. For example, the reader badge 425 may create a reader message 430 including the tag identifying information 415 and the tag-type identifying information 420 included in the beacon message 410 and append example badge identifying information 435, an example timestamp 440, example signal strength information 445, and example channel identifying information 450. In the illustrated example, the badge identifying information 435 is a string of alphanumeric characters that uniquely identifies the reader badge 410 (e.g., a MAC address, a serial number, an alphanumeric signature, etc.). The example timestamp 440 identifies a date and/or time (e.g., Jan. 1, 2015, 9:10:04 pm) when the beacon message 410 was received by the reader badge 425. The example signal strength information 445 identifies signal strength of the beacon message 410 when it was received by the reader badge 425 (e.g., a received signal strength indication (RSSI) value). The example channel identifying information 450 identifies a channel on which the beacon message 410 was received (e.g., a Bluetooth frequency channel such as channel 37, channel 38 or channel 39).

In the illustrated example of FIG. 4, the reader badge 425 periodically communicates a group (e.g., a batch) of reader messages 430 to the RTLS server 455. For example, the reader badge 425 may transmit one or more reader messages 430 that were collected over a period of time (e.g., thirty seconds). Additionally or alternatively, the reader badge 425 may communicate one or more reader message(s) 430 aperiodically and/or as a one-time event. For example, the reader badge 425 may collect a threshold number of reader messages 430 prior to transmitting the collected reader messages 430 to the RTLS server 455. In some examples, the reader badge 425 transmits the reader messages 430 as they are created by the reader badge 425.

In the illustrated example of FIG. 4, the RTLS server 455 is a server and/or database that facilitates proximity detection and location tracking. In some examples, the RTLS server 455 is implemented using multiple devices. For example, the RTLS server 455 may include disk arrays or multiple workstations (e.g., desktop computers, workstation servers, laptops, etc.) in communication with one another.

In the illustrated example, the RTLS server 455 is in communication with the reader badge 425 via one or more wireless networks represented by example network 460. Example network 460 may be implemented using any suitable wireless network(s) including, for example, one or more data busses, one or more wireless Local Area Networks (LANs), one or more cellular networks, the Internet, etc. As used herein, the phrase "in communication," including variances thereof (e.g., communicates, in communication with, etc.), encompasses direct communication and/or indirect communication through one or more intermediary components and does not require direct physical (e.g., wired) communication and/or constant communication, but rather additionally includes communication at periodic or aperiodic intervals, as well as one-time events.

In the illustrated example of FIG. 4, the RTLS server 455 utilizes the reader messages 430 to facilitate proximity detection and location tracking of assets in the environment 400. In the illustrated example, the RTLS server 455 selects a portion of reader messages 430 received from the reader badge 425 to determine a location of the reader badge 425. For example, the RTLS server 455 may process the reader messages 430 to identify a first subset of reader messages 430 (e.g., one or more reader messages) that were received by the reader badge 425 during a first window of interest (e.g., a five second window) and that were fixed-location asset tag type (e.g., based on the tag-type information 420 included in the first subset of reader messages). In the illustrated example of FIG. 4, the RTLS server 455 utilizes the signal strength information 445 included in the first subset of reader messages 430 to determine a nearest fixed-location asset. For example, a relatively stronger RSSI value may indicate that the broadcasting beacon tag 405 is closer in proximity to the reader badge 425 than a beacon tag 405 associated with a relatively weaker RSSI value. In the illustrated example of FIG. 4, the RTLS server 455 updates the location of the reader badge 425 based on the nearest fixed-location asset.

In the illustrated example of FIG. 4, once the RTLS server 455 associates the reader badge 425 with a location (e.g., the location of the nearest fixed-location asset), the RTLS server 455 identifies a second subset of reader messages 430 (e.g., one or more reader messages) that were received by the reader badge 425 during the first window of interest (e.g., a five second window) and that were mobile-location asset tag type (e.g., based on the tag-type information 420 included in the second subset of reader messages 430). For example, the RTLS server 455 may update the location of a mobile-location asset based on its proximity to the reader badge 425.

In the illustrated example of FIG. 4, the RTLS server 455 selects a reader message of the second subset of reader messages 430 and classifies the corresponding mobile-location assets relative location to the reader badge 425 based on the RSSI value 455 included in the selected reader badge 430. For example, the RTLS server 455 classifies mobile-location asset as relatively-far assets when the signal strength information 455 satisfies a first threshold (e.g., the RSSI value is less than (−60) decibels). The example RTLS server 455 of FIG. 4 classifies mobile-location assets as relatively-immediate assets when the signal strength information 455 satisfies a second threshold (e.g., the RSSI value is greater than (−40) decibels). In the illustrated example of FIG. 4, the RTLS server 455 classifies mobile-location assets as relatively-near assets when the signal strength information 455 does not satisfy the first threshold and the second threshold. For example, the RTLS server 455 may classify mobile-location assets as relatively-near assets when the RSSI value is less than (−40) decibels and greater than (−60) decibels.

In the illustrated of FIG. 4, depending on the relative location classifications, the RTLS server 455 updates the location of the mobile-location asset and/or updates an asset-location confidence score associated with the mobile-location asset. In the illustrated example, the asset-location confidence score represents a probability (or likelihood) that a mobile-location asset may be found at the currently assigned asset-location. For example, when a mobile-location asset is "seen" in the same location, the RTLS server 455 increases the asset-location confidence score of the mobile-location asset. When the mobile-location asset is "seen" in a different location, the RTLS server 455 decreases the asset-location confidence score of the mobile-location asset. Additionally, when the asset-location confidence score fails to satisfy a location threshold (e.g., is less than a location threshold), the asset-location of the mobile-location asset may be updated based on, for example, the location of the reader badge 425 that collected the beacon message 410 emitted from the mobile-location asset (e.g., by the beacon tag 405 affixed to the mobile-location asset).

In the illustrated example, when a mobile-location asset is classified as relatively-far, the example RTLS server 455 of FIG. 4 discards the reader message 430 and the RTLS server 455 makes not change to the location of the mobile-location asset and/or the asset-location confidence score associated with the mobile-location asset. For example, the reader badge 425 may have collected a relatively weak beacon message emitted from a mobile-location asset passing through the hallway outside of the patient room #1. In some examples, the reader badge 425 may filter such beacon messages (e.g., beacon messages 410 that are associated with weak (e.g., low) RSSI values) rather than communicate the weak beacon messages to the RTLS server 455.

When a mobile-location asset is classified as a relatively-immediate asset, high signal strength (e.g., an RSSI value greater than (−40) decibels) may be indicative of a mobile-location asset that is in-front of the hospital worker 426, is being used by the hospital worker 426 and/or is being moved by the hospital worker 426. In some such instances, the location of the mobile-location asset may be assumed to be the same as the location of the reader badge 425. In the illustrated example, the example RTLS server 455 of FIG. 4 updates the location of the mobile-location asset to the location of the reader badge 425. In addition, the example RTLS server 455 increments the asset-location confidence score of the mobile-location asset (e.g., the probability of the mobile-location asset being located at the updated asset-location is increased). In some examples, if the beacon tag 405 is relatively-immediate to the reader badge 425, an assumption may be made that the caregiver is interacting with the corresponding assets. For example, the caregiver may be pushing a patient in a wheelchair.

In the illustrated example of FIG. 4, when a mobile-location asset is classified as a relatively-near asset (e.g., is associated with a medium signal strength), the example RTLS server 455 of FIG. 4 compares the current location associated with the mobile-location asset to the location of the reader badge 425. In the illustrated example, the RTLS server 455 increases the asset-location confidence score of the mobile-location asset when the current asset-location is the same as the location of the reader badge 425. For example, the mobile-location asset is "seen" in the same location as it is currently assigned. In some examples when the current asset-location is not the same as the location of the reader badge 425, the example RTLS server 455 decreases the asset-location confidence score of the mobile-location asset. In addition, the example RTLS server 455 compares the asset-location confidence score of the mobile-location asset to a location threshold and, when the asset-location confidence score fails to satisfy the location threshold (e.g., is less than the location threshold), the RTLS server 455 updates the asset-location of the mobile-location asset to the location of the reader badge 425 that received the corresponding beacon message 410.

In the illustrated example of FIG. 4, the example environment 400 includes an example dock module 465. The example dock module 465 may be used to charge one or more reader badges 425. In some examples, the dock module 465 receives beacon messages 410 from beacon tags 405 and/or transmits reader messages 430 to the RTLS server 455.

Figure 5:
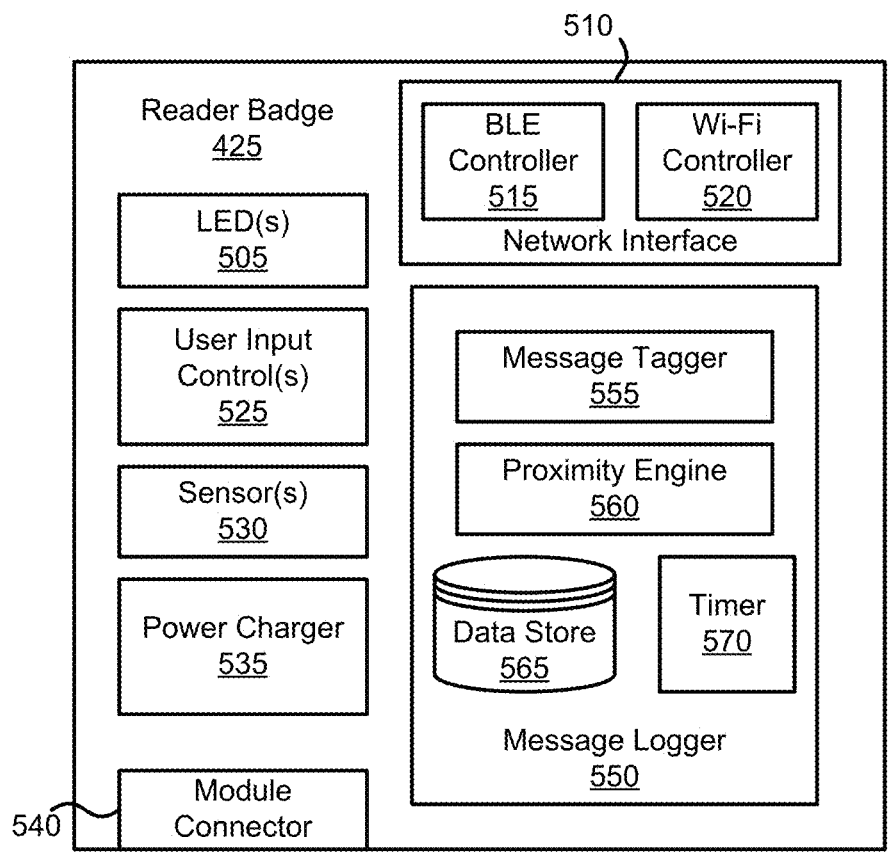
FIG. 5 is a block diagram of the example reader badge of the example environment of FIG. 4.

FIG. 5 is a block diagram of the example reader badge 425 of FIG. 4. The example reader badge 425 of FIG. 5 includes example light-emitting diodes (LEDs) 505 to indicate status information. For example, the LEDs 505 may indicate when the battery charge of the reader badge 425 is low, when the reader badge 425 is connected to the example RTLS server 455 and/or is transmitting information (e.g., the example reader message(s) 430) via the wireless network 460, when the reader badge 425 is receiving and/or processing beacon messages 410, etc.

In the illustrated example of FIG. 5, the example reader badge 425 includes an example network interface 510 to facilitate collecting the beacon messages 410 and/or transmitting the reader messages 430. For example, the reader badge 425 may receive (e.g., collect, detect, capture, obtain, etc.) the beacon messages 410 via an example BLE controller 515 and/or an infrared (IR) sensor. The example network interface 510 of FIG. 5 also includes one or more Wi-Fi controller(s) 520 to communicate with a wireless network (e.g., the example network 460 of FIG. 4). For example, the reader badge 425 may communicate one or more reader message(s) 430 to the RTLS server 455 via a wireless infrastructure such as the example network 460.

The example reader badge 425 of FIG. 5 includes example user-input controls 525 (e.g., buttons) to facilitate control of the reader badge 425. The example reader badge 425 includes one or more sensor(s) 530 to manage power utilization of the reader badge 425. In some examples, the sensors 530 may include a motion sensor and an internal measurement (IMU) controller (e.g., a gyroscope processor). For example, the motion sensor and/or the IMU controller may determine when the reader badge 425 is at rest (e.g., placed on a table) for a period and transition the reader badge 425 from a normal power utilization state to a low-power utilization state (e.g., a sleep state). The motion sensor and/or the IMU controller may transition the reader badge 425 to a normal power utilization state when the reader badge 425 is not at rest (e.g., moving with a caregiver). In some examples, transitioning the reader badge 425 to the low-power utilization state may include turning the beacon message receiving transceiver (e.g., the BLE controller 515) off and/or the reader message communicating controller (e.g., the Wi-Fi controller 520) to conserve power.

The example reader badge 425 of FIG. 5 includes power charging circuitry 535 to manage charging the reader badge 425 when connected to a power source such as the example dock module 465 of FIG. 4. The example power charging circuitry 535 may also include a power source (e.g., one or more batteries) to supply power to the reader badge 425.

Figure 7:
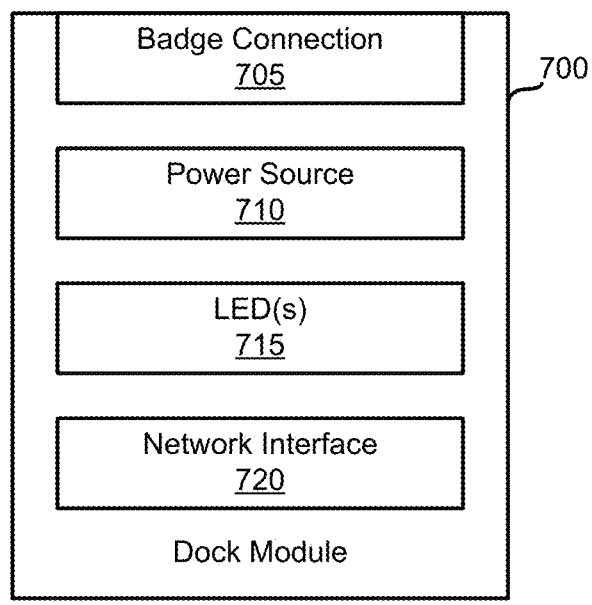
FIG. 7 is a block diagram of the example dock module of the example environment of FIG. 4.

The example reader badge 425 of FIG. 5 also includes an example module connector 540 to connect the reader badge 425 to an example dock module (e.g., an example dock module 465 described below in connection with FIG. 7). In the illustrated example, the example module connector 540 is an example micro USB connection to couple the reader badge 425 to the dock module 465.

In the illustrated example of FIG. 5, the reader badge 425 includes an example message logger 550 to record collected beacon messages. For example, the reader badge 425 may record one or more beacon messages and communicate reader messages to the RTLS server 455 in batches. In the illustrated example of FIG. 5, the reader badge 425 communicates a batch of reader messages 430 to the RTLS server 455 when a threshold interval of time is satisfied. For example, the reader badge 425 may collect beacon messages 410 and transmit a batch of reader messages 430 collected during five second intervals. However, other implementations are additionally or alternatively possible. For example, the reader badge 425 may collect a threshold number (e.g., 10 beacon messages) before transmitting a batch of 10 corresponding reader messages 430 to the RTLS server 455. Additionally or alternatively, the reader badge 425 may transmit a reader message 430 once generated (e.g., after appending reader information).

In the illustrated example of FIG. 5, the message logger 550 includes an example message tagger 555, an example proximity engine 560, an example data store 565 and an example timer 570. The example message logger 550 includes the message tagger 555 to record collected beacon messages 410 and to append reader badge information to the collected beacon messages 410. For example, the message tagger 555 may record the tag identifying information 415 and the tag-type identifying information 420 of the collected beacon message 410 in the example data store 560. The example message tagger 555 may also append the reader identifying information 455 associated with the reader badge 425, the timestamp 440 identifying when the beacon message 410 was collected by the reader badge 425, the signal strength information 445 and the channel identifying information 450. An example data table 800 representing collected beacon messages is shown in FIG. 8.

In the illustrated example of FIG. 5, the message logger 550 includes the proximity engine 560 to determine proximity of the reader badge 425 to the source beacon tag based on the signal strength information 445. For example, if the RSSI strength satisfies a proximity threshold (e.g., the RSSI strength is at least a minimum threshold strength), the proximity engine 560 determines the source beacon tag is a proximate beacon tag (e.g., the beacon tag 405 is relatively-near or relatively-immediate). In some such examples, the proximity engine 560 discards the received beacon message when the RSSI strength does not satisfy the proximity threshold. Using the comparison results of the RSSI strength and the proximity threshold, the example proximity engine 560 of FIG. 5 may filter beacon messages which may be broadcast by source beacon tags located within the environment but to which the caregiver is not proximate. For example, the hospital worker 426 may be positioned in one corner of a patient room and the reader badge 425 may receive a faint beacon message 410 from a beacon tag 505 positioned in the hallway outside of the patient room.

In the illustrated example, the reader messages 430 are stored in the example data store 565 of FIG. 5. As described above, the reader messages 430 are the information 415, 420 included in the beacon tag 410 and the information 435, 440, 445, 450 appended by the example message tagger 555. The example data store 565 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., a flash memory). The example data store 565 may additionally or alternatively be implemented by one or more double data rate (DDR) memories such as DDR, DDR2, DDR3, mobile DDR (mDDR), etc. The example data store 565 may additionally or alternatively be implemented by one or more mass storage devices such as hard disk drive(s), compact disk drive(s), digital versatile disk drive(s), etc. While in the illustrated example the example data store 565 is illustrated as a single database, the data store 565 may be implemented by any number and/or type(s) of databases.

The example message logger 550 includes the example timer 570 to initiate transmitting a batch of reader messages 430 to the RTLS server 455. For example, when the timer 570 expires, the example message logger 550 may cause the reader messages 430 stored in the data store 565 to be communicated to the RTLS server 455 via, for example, the Wi-Fi controller 520.

Figure 6:
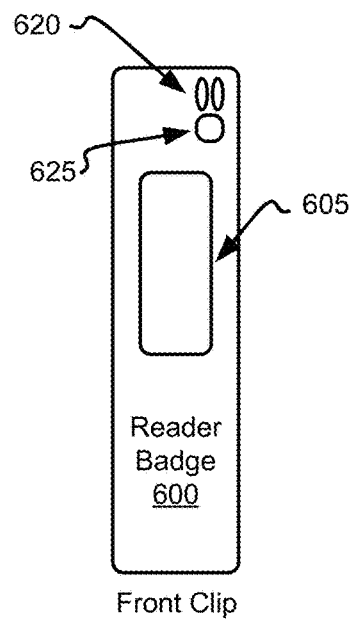
FIG. 6 illustrates another example reader badge, according to the present disclosure.
Figure 6:
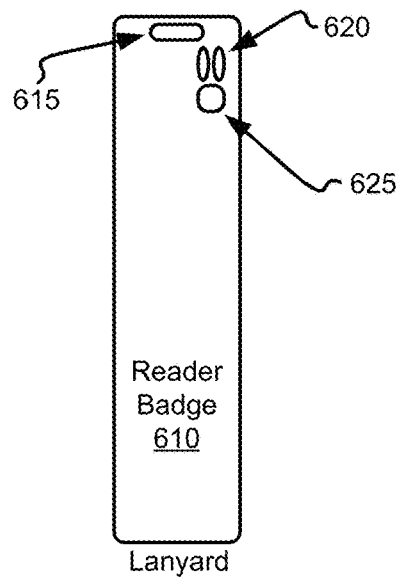

FIG. 6 illustrates a front clip reader badge 600 having an example front clip 605. FIG. 6 also illustrates an example lanyard reader badge 610 having an example lanyard receiver 615. The example reader badges 600, 610 of FIG. 6 also include LEDs 620 and an IR sensor 625.

As described above, the example reader badge 425 may additionally or alternatively be coupled (e.g., mechanically coupled, electronically coupled, etc.) to the example dock module 465. In the illustrated example of FIG. 7, the dock module 465 may be used to charge one or more reader badges 425. For example, the dock module 465 may be placed at nursing stations, break rooms, hallways, etc. A hospital worker may couple their reader badge 425 to the dock module 465, via an example badge connection 705, when they are off-duty. In the illustrated example of FIG. 7, the dock module 465 includes an external power source 710 (e.g., an AC/DC connection) to draw power from and to charge one or more connected reader badges 425 and one or more example LEDs 715 to indicate when a reader badge 425 is coupled to the dock module 465, when the reader badge 425 is charging, when the reader badge 425 is assigned to a caregiver, etc.

In some examples, the dock module 465 may operate as a fixed-location reader badge. In the illustrated example of FIG. 7, the example dock module 465 includes an example network interface 720 to receive beacon messages and/or to transmit reader messages. For example, the network interface 720 may include a BLE controller and/or an IR sensor to receive the example beacon messages 410 broadcast by beacon tags 405. The example network interface 720 may additionally or alternatively include a Wi-Fi controller to transmit reader messages 430 to the RTLS server 455 via, for example, the example network 460. In some examples, the dock module 465 may generate reader messages 430 and transmit the generated reader messages 430 to the RTLS server 455. In some examples, the dock module 465 may receive reader messages 430 from a reader badge 425 and transmit the received reader messages 430 to the RTLS server 455. For example, when a reader badge 425 is docked with the dock module 465, the example dock module 465 may collect reader messages 430 transferred to the dock module 465 by the reader badge 425 via the example network interface 720.

In some examples, the dock module 465 may be associated with a fixed-location. For example, when a dock module 465 is positioned in a receptionist area, the location of the dock module 465 may be assigned to the receptionist area (e.g., a counter #1 in the receptionist area). In some examples, similar to the reader badges 425, the location of the dock module 465 may depend on the location of the nearest fixed-location asset beacon tag.

FIG. 8 illustrates an example data table 800 that may be stored by the example data store 565 of FIG. 5 to store beacon messages collected by the reader badge 425. For example, the example message logger 550 may log the beacon messages 410 when received. In the illustrated example, the message logger 550 appends reader information to the beacon messages.

The example data table 800 includes an example tag identifier column 805, an example tag-type identifier column 810, an example timestamp column 815, an example RSSI value identifying column 820 and an example channel number identifying column 825. The example tag identifier column 805 indicates the beacon tag 405 that broadcast the corresponding beacon message 410. The example tag-type identifier column 810 indicates the tag-type of the beacon tag. For example, the tag-type identifier column 810 may indicate whether the beacon tag is affixed to a fixed-location asset or to a mobile-location asset. The example timestamp column 815 indicates when (e.g., a date and/or time) when the corresponding beacon message 410 was received. The example RSSI value identifying column 820 indicates the signal strength (e.g., power level) of the received beacon message 410. The example channel number identifying column 825 indicates a channel on which the beacon message 410 was received (e.g., a Bluetooth frequency channel such as channel 37, channel 38 or channel 39). However, any other columns representing any other conditions and/or characteristics of the access request may additionally or alternatively be used. Moreover, the example column(s) of the example data table 800 may be implemented in any other fashion (e.g., using a different data structure).

The example data table 800 of the illustrated example of FIG. 8 includes three example rows 850, 855, 860 corresponding to three different beacon messages collected by the reader badge 425. The example first row 850 indicates that a beacon message was received from a beacon tag ("Entry_1") that is affixed to a "fixed-location asset" at "0:00:01." In addition, the signal strength of the beacon message corresponding the example first row 850 was "high" (e.g., was greater than (−40) decibels) and was received on channel number "37."

The example second row 855 indicates that a beacon message was received from a beacon tag ("Chair_1") that is affixed to a "mobile-location asset" at "0:00:02." In addition, the signal strength of the beacon message corresponding the example second row 855 was "low" (e.g., was less than (−60) decibels) and was received on channel number "37."

The example third row 860 indicates that a second beacon message was received from the beacon tag ("Chair_1") that is affixed to a "mobile-location asset" at "0:00:03." In addition, the signal strength of the beacon message corresponding the example third row 860 was "med" (e.g., was greater than (−60) decibels and less than (−40) decibels) and was received on channel number "38." While three example collected beacon messages are represented in the example data table 800 of FIG. 8, more or fewer beacon messages may be collected.

While an example manner of implementing the reader badge 425 of FIG. 4 and/or the example reader badges 600, 610 of FIG. 6 is illustrated in FIG. 5, one or more of the elements, processes and/or devices illustrated in FIG. 5 may be combined, divided, re-arranged, omitted, eliminated and/or implemented in any other way. Further, the example network interface 510, the example BLE controller 515, the example Wi-Fi controller 520, the example sensor(s) 530, the example power charger 535, the example message logger 550, the example message tagger 555, the example proximity engine 560, the example data store 565, the example timer 570 and/or, more generally, the example reader badge 425 of FIG. 4 and/or the example reader badges 600, 610 of FIG. 6 may be implemented by hardware, software, firmware and/or any combination of hardware, software and/or firmware. Thus, for example, any of the example network interface 510, the example BLE controller 515, the example Wi-Fi controller 520, the example sensor(s) 530, the example power charger 535, the example message logger 550, the example message tagger 555, the example proximity engine 560, the example data store 565, the example timer 570 and/or, more generally, the example reader badge 425 of FIG. 4 and/or the example reader badges 600, 610 of FIG. 6 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example network interface 510, the example BLE controller 515, the example Wi-Fi controller 520, the example sensor(s) 530, the example power charger 535, the example message logger 550, the example message tagger 555, the example proximity engine 560, the example data store 565, the example timer 570 and/or, more generally, the example reader badge 425 of FIG. 4 and/or the example reader badges 600, 610 of FIG. 6 is/are hereby expressly defined to include a tangible computer readable storage device or storage disk such as a memory, a digital versatile disk (DVD), a compact disk (CD), a Blu-ray disk, etc. storing the software and/or firmware. Further still, the example reader badge 425 of FIG. 4 and/or the example reader badges 600, 610 of FIG. 6 may include one or more elements, processes and/or devices in addition to, or instead of, those illustrated in FIG. 5, and/or may include more than one of any or all of the illustrated elements, processes and devices.

Figure 9:
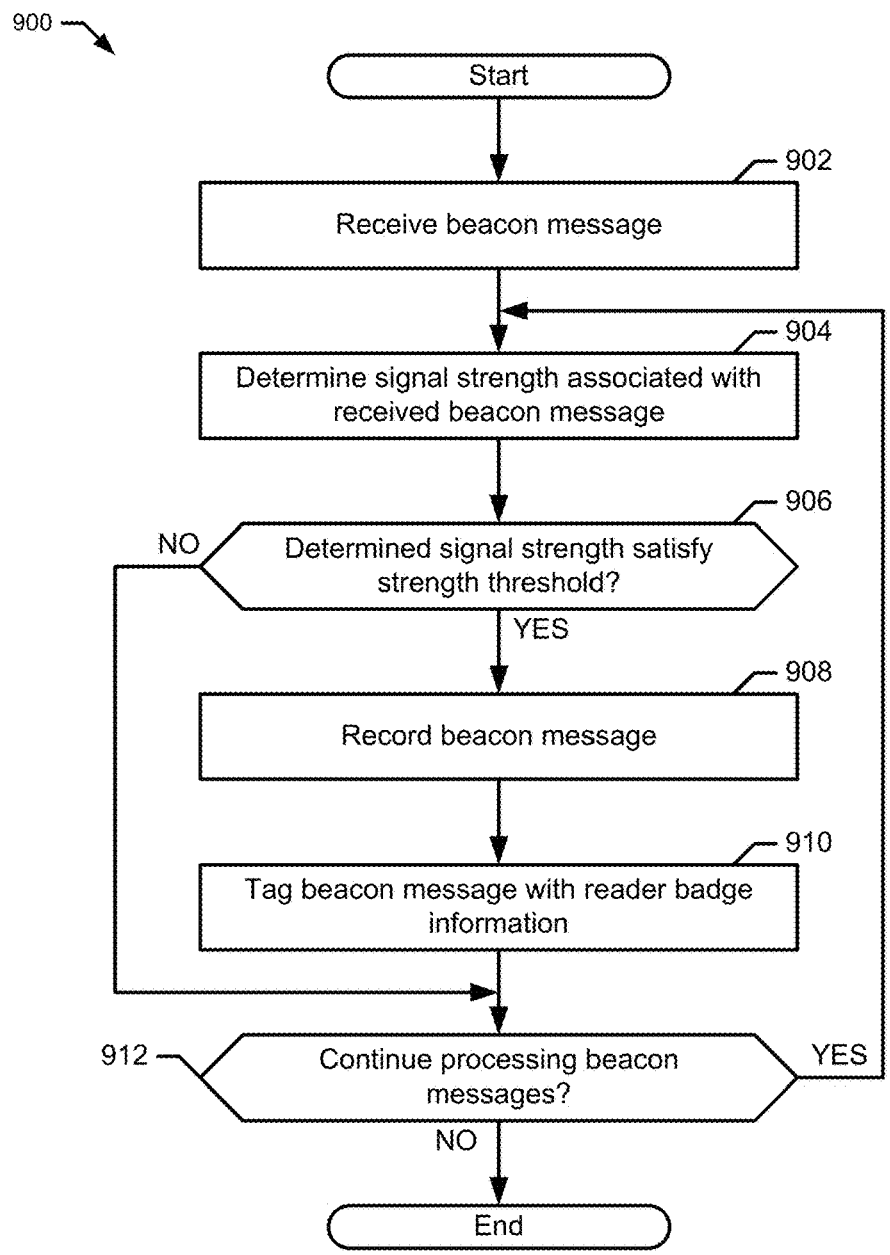
FIG. 9 is a flowchart representative of example machine-readable instructions that may be executed to log collected beacon messages in the environment of FIG. 4.
Figure 10:
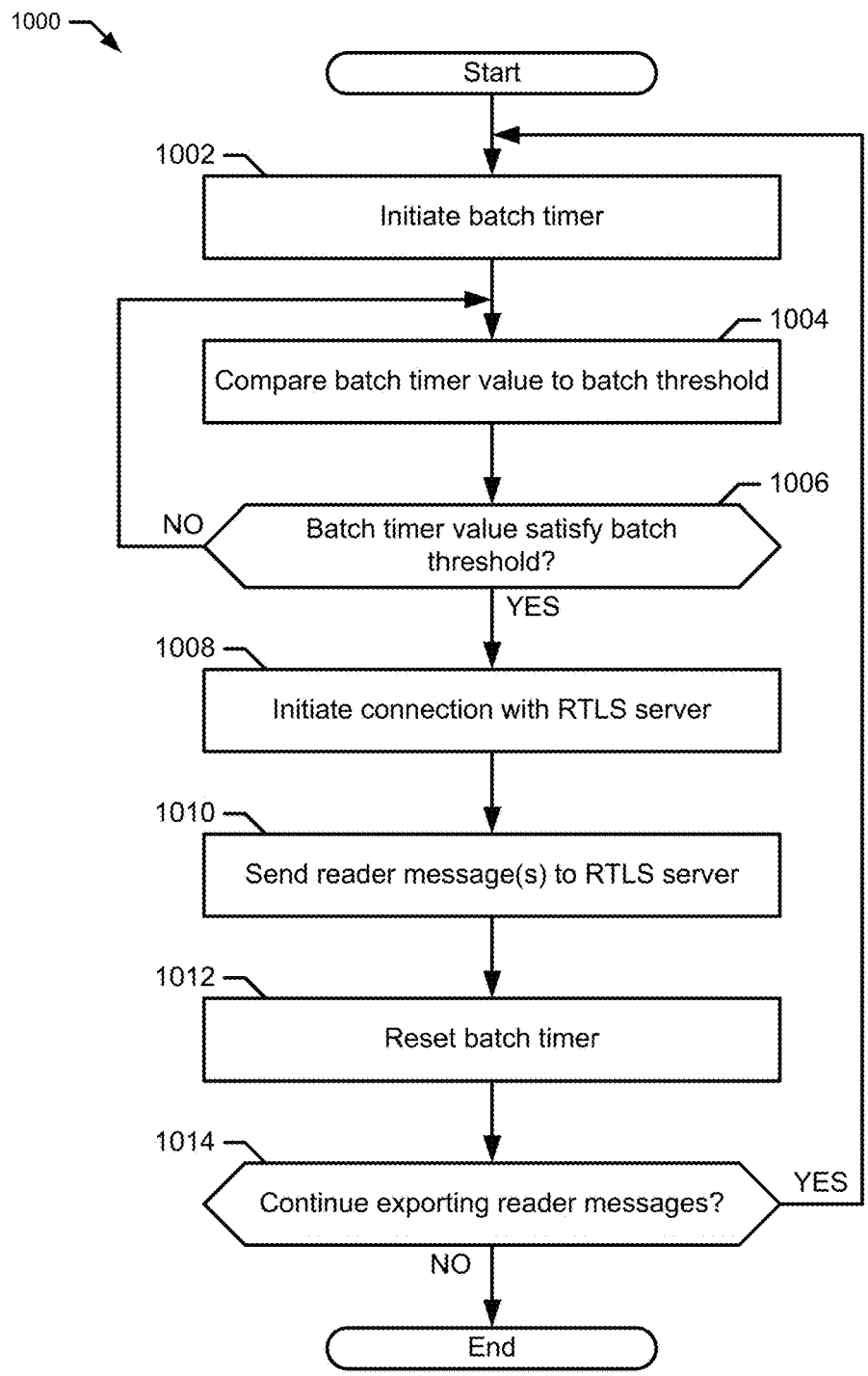
FIG. 10 is a flowchart representative of example machine-readable instructions that may be executed to export reader messages in the environment of FIG. 4.

Flowcharts representative of example machine-readable instructions for implementing the example reader badge 425 of FIGS. 4 and/or 5, and/or the example reader badges 600, 610 of FIG. 6 are shown in FIGS. 9 and 10. In these examples, the machine-readable instructions comprise a program(s) for execution by a processor such as the processor 1112 shown in the example processor platform 1100 discussed below in connection with FIG. 11. The program(s) may be embodied in software stored on a tangible computer readable storage medium such as a CD-ROM, a floppy disk, a hard drive, a digital versatile disk (DVD), a Blu-ray disk, or a memory associated with the processor 1112, but the entire program(s) and/or parts thereof could alternatively be executed by a device other than the processor 1112 and/or embodied in firmware or dedicated hardware. Further, although the example program(s) is/are described with reference to the flowcharts illustrated in FIGS. 9 and/or 10, many other methods of implementing the example reader badge 425 of FIGS. 4 and/or 5, and/or the example reader badges 600, 610 of FIG. 6 may alternatively be used. For example, the order of execution of the blocks may be changed, and/or some of the blocks described may be changed, eliminated, or combined.

As mentioned above, the example processes of FIGS. 9 and/or 10 may be implemented using coded instructions (e.g., computer and/or machine-readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine-readable storage medium" are used interchangeably. Additionally or alternatively, the example processes of FIGS. 9 and/or 10 may be implemented using coded instructions (e.g., computer and/or machine-readable instructions) stored on a non-transitory computer and/or machine-readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. Comprising and all other variants of "comprise" are expressly defined to be open-ended terms. Including and all other variants of "include" are also defined to be open-ended terms. In contrast, the term consisting and/or other forms of consist are defined to be close-ended terms.

FIG. 9 is a flowchart representative of example machine-readable instructions 900 that may be executed to implement the example reader badge 425 of FIGS. 4, 5 and/or 6 to process received beacon messages 410. The example instructions 900 of the illustrated example of FIG. 9 begin at block 902 when the example reader badge 425 receives the beacon message 410. For example, the BLE controller 515 (FIG. 5) may collect the beacon message 410 broadcast by beacon tag. At block 904, the example reader badge 425 determines the signal strength of the beacon message 410. For example, the example message tagger 555 (FIG. 5) may determine the RSSI value of the beacon message 410 when it was received. At block 906, the example reader badge 425 determines whether the signal strength satisfies a strength threshold. For example, the example proximity engine 560 (FIG. 5) may compare the RSSI value to a minimum signal strength threshold (e.g., (−60) decibels). If, at block 906, the example proximity engine 560 determined that the signal strength satisfied the strength threshold, then, at block 908, the example reader badge 425 records the beacon message. For example, the example message tagger 555 may record the tag identifying information 415 and the tag-type identifying information 420 in the example data store 565 (FIG. 5). At block 910, the example reader badge 425 tags the beacon message with reader badge information. For example, the message tagger 555 may append the reader identifying information 435 of the reader badge 425, the timestamp 440 identifying when the beacon message 410 was received, the signal strength information 445 and the channel identifying information 450.

If, at block 906, the example reader badge 425 determined that the signal strength did not satisfy the strength threshold, or, after, at block 910, the example reader badge 425 tags the beacon message 430 with the reader badge information 435, 440, 445, 450, then, at block 912, the example reader badge 425 determines whether to continue processing beacon messages. For example, the reader badge 425 may determine whether another beacon message was received. If, at block 912, the reader badge 425 determined to continue processing beacon messages, control returns to block 902 to receive another beacon message.

If, at block 912, the example reader badge 425 determined to stop processing beacon messages, the example program 900 of FIG. 9 ends.

FIG. 10 is a flowchart representative of example machine-readable instructions 1000 that may be executed to implement the example reader badge 425 of FIGS. 4, 5 and/or 6 to export reader messages. The example instructions 1000 of the illustrated example of FIG. 10 begin at block 1002 when the example reader badge 425 initiates a batch timer. For example, the reader badge 425 may initiate the example timer 570 (FIG. 5). At block 1004, the example reader badge 425 compares the batch timer value to a batch threshold. For example, the reader badge 425 may transmit one or more received messages to the RTLS server 455 (FIG. 5) every five seconds. If, at block 1006, the example timer 570 determined that the batch timer value did not satisfy the batch threshold (e.g., was less than five seconds), then control returns to block 1004 to compare the batch time value to the batch threshold.

If, at block 1006, the example reader badge 425 determined that the batch timer value satisfied the batch threshold (e.g., was equal to or greater than five seconds), then, at block 1008, the example reader badge 425 initiates a connection with the RTLS server 455. For example, the message logger 540 may cause the example Wi-Fi controller 520 to initiate a connection with the RTLS server 455. At block 1010, the example reader badge 425 sends the one or more reader message(s) 430 of the batch to the RTLS server 455. In some examples, the reader badge 425 may transmit the one or more reader message(s) 430 via web service calls (e.g., HTTP(S) requests, etc.). At block 1012, the example reader badge 425 resets the batch timer 570. At block 1014, the example reader badge 425 determines whether to continue exporting reader messages to the RTLS server 455. If, at block 1014, the example reader badge 425 determined to continue exporting reader messages, then control returns to block 1002 to initiate the batch timer 570. If, at block 1014, the example reader badge 425 determined not to continue exporting reader messages to the RTLS server 455, the example program 1000 of FIG. 10 ends.

Figure 11:
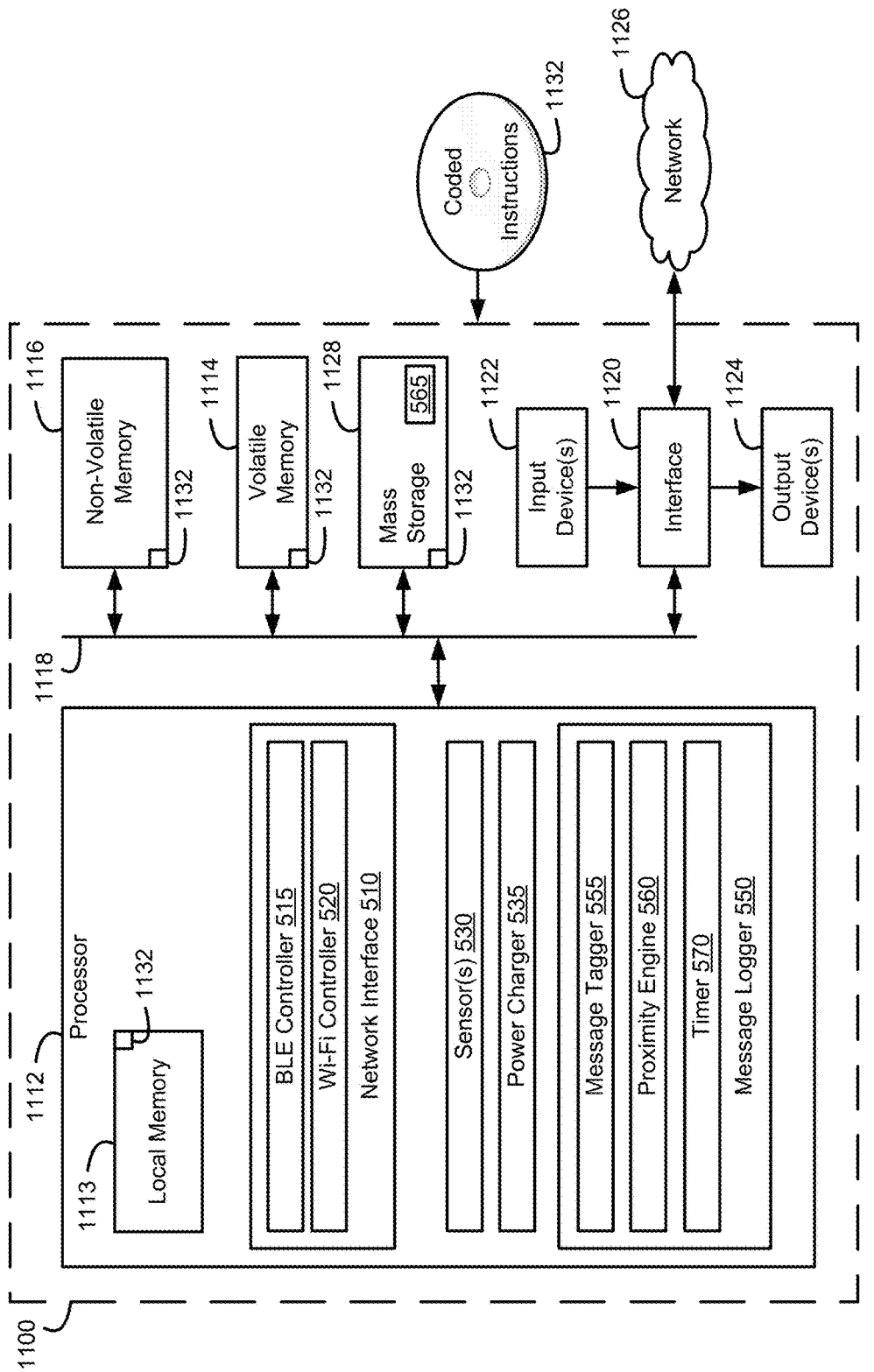
FIG. 11 is a block diagram of an example reader badge structured to execute the example machine-readable instructions of FIGS. 9 and/or 10 to implement the example reader badge of FIG. 4.

FIG. 11 is a block diagram of an example processor platform 1100 capable of executing the instructions of FIGS. 9 and/or 10 to implement the example reader badge 425 of FIGS. 4 and/or 5, and/or the example reader badges 600, 610 of FIG. 6. The processor platform 1100 can be, for example, a server, a personal computer, or any other type of computing device.

The processor platform 110 of the illustrated example includes a processor 1112. The processor 1112 of the illustrated example is hardware. For example, the processor 1112 can be implemented by one or more integrated circuits, logic circuits, microprocessors or controllers from any desired family or manufacturer.

The processor 1112 of the illustrated example includes a local memory 1113 (e.g., a cache). The processor 1112 of the illustrated example executes the instructions to implement the example network interface 510, the example BLE controller 515, the example Wi-Fi controller 520, the example sensor(s) 530, the example power charger 535, the example message logger 550, the example message tagger 555, the example proximity engine 560, the example data store 565, the example timer 570 and/or, more generally, the example reader badge 425 of FIGS. 4 and/or 5, and/or the example reader badges 600, 610 of FIG. 6. The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1120 of the illustrated example, thus, typically includes a graphics driver card, a graphics driver chip or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives. The example mass storage 1128 implements the example data store 565.

The coded instructions 1132 of FIGS. 9 and/or 10 may be stored in the mass storage device 1128, in the volatile memory 1114, in the non-volatile memory 1116, and/or on a removable tangible computer readable storage medium such as a CD or DVD.

Figure 12:
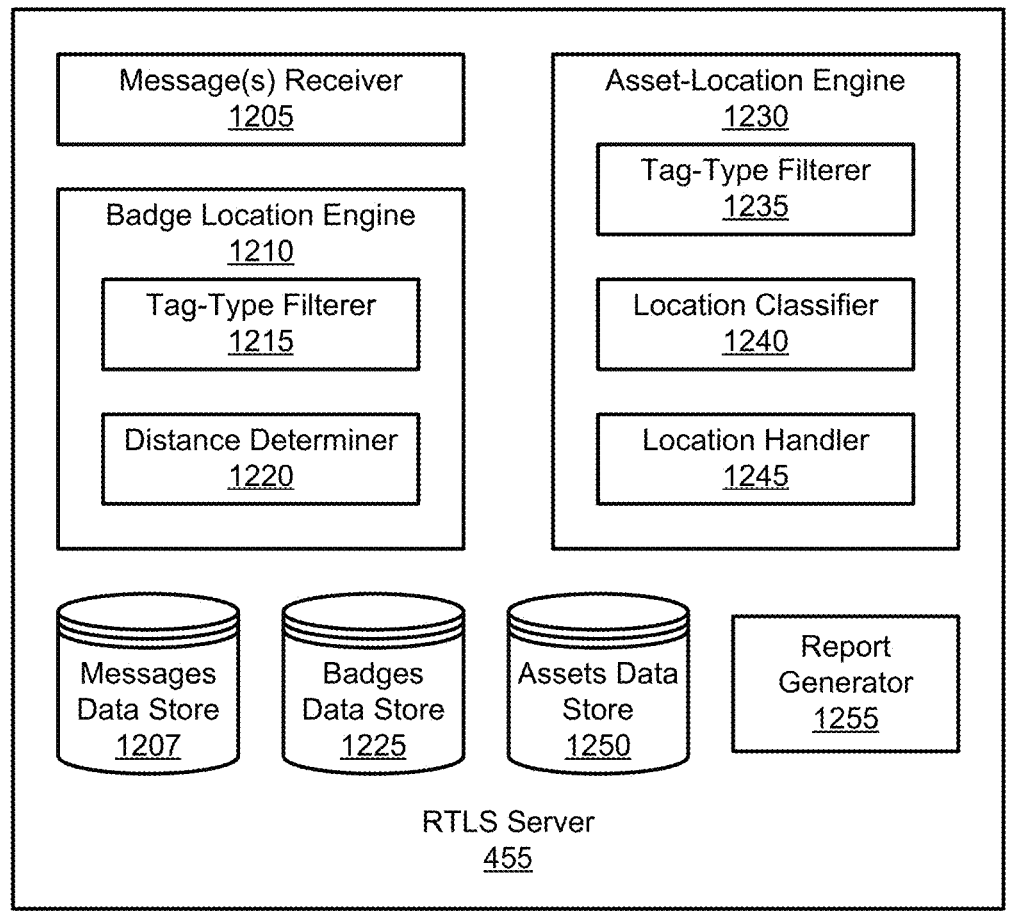
FIG. 12 is a block diagram of the example real-time location services (RTLS) server of the example environment of FIG. 4.

FIG. 12 is a block diagram of the example RTLS server 455 of FIG. 4. The example RTLS server 455 includes an example message(s) receiver 1205, an example messages data store 1207, an example badge location engine 1210, an example badges data store 1225, an example asset-location engine 1230, an example assets data store 1250 and an example report generator 1255. The example message(s) receiver 1205 of FIG. 12 receives one or more reader message(s) 430 from the reader badge 425. In the illustrated example of FIG. 12, the message(s) receiver 1205 receives a batch (e.g., one or more) reader message(s) 430 periodically. For example, the message(s) receiver 1205 may receive the batch of reader messages 430 after five second intervals. Additionally or alternatively, the example message(s) receiver 1205 may receive the batch of reader message(s) 430 aperiodically (e.g., as they are created by the example reader 425) and/or as a one-time event.

In the illustrated example, the message(s) receiver 1205 stores the received reader messages 430 in the example messages data store 1207 of FIG. 12. As described above, the reader messages 430 are the information 415, 420 included in the beacon tag 410 and the information 435, 440, 445, 450 appended by the example reader badge 425. An example data table 1300 representing received reader messages is shown in FIG. 13. The example messages data store 1207 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., a flash memory). The example messages data store 1207 may additionally or alternatively be implemented by one or more double data rate (DDR) memories such as DDR, DDR2, DDR3, mobile DDR (mDDR), etc. The example messages data store 1207 may additionally or alternatively be implemented by one or more mass storage devices such as hard disk drive(s), compact disk drive(s), digital versatile disk drive(s), etc. While in the illustrated example the messages data store 1207 is illustrated as a single database, the messages data store 1207 may be implemented by any number and/or type(s) of databases.

In the illustrated example of FIG. 12, the example RTLS server 455 includes the example badge location engine 1210 to associate the reader badges 425 with corresponding locations. For example, the badge location engine 1210 may identify the nearest beacon tag to the reader badge 425 and associate the location of the nearest beacon tag with the reader badge 425. In the illustrated example of FIG. 12, the badge location engine 1210 includes an example tag-type filterer 1215 and an example distance determiner 1220.

The example badge location engine 1210 of FIG. 12 includes the tag-type filterer 1215 to process the messages logged in the messages data store 1207 and identify the reader messages 430 associated with fixed-location assets. For example, the tag-type filterer 1215 may parse the tag-type identifying information 420 included in the reader messages 430 to identify the fixed-location asset reader messages. In some examples, the tag-type filterer 1215 may log the identified fixed-location asset reader messages in the badges data store 1225.

The example badge location engine 1210 of FIG. 12 includes the distance determiner 1220 to parse the reader messages 430 identified by the tag-type filterer 1215 and associate the location of the nearest beacon tag with the reader badge 425. For example, the distance determiner 1220 may parse the signal strength information 445 of the fixed-location asset reader messages 430 and identify the reader message associated with the strongest (e.g., largest) RSSI value. In the illustrated example of FIG. 12, the distance determiner 1220 associates the beacon tag corresponding to the reader message with the strongest RSSI value as the nearest beacon tag to the reader badge 425. However, other techniques for determining the nearest beacon tag may additionally or alternatively be utilized. In the illustrated example, the distance determiner 1220 associates the fixed-location associated with the beacon tag with the location of the reader badge 425.

In the illustrated example, the badge location engine 1210 stores the determined reader badge-location mappings in the example badges data store 1225 of FIG. 12. An example data table 1400 representing reader badges and their associated location mappings is shown in FIG. 14. The example badges data store 1225 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., a flash memory). The example badges data store 1225 may additionally or alternatively be implemented by one or more double data rate (DDR) memories such as DDR, DDR2, DDR3, mobile DDR (mDDR), etc. The example badges data store 1225 may additionally or alternatively be implemented by one or more mass storage devices such as hard disk drive(s), compact disk drive(s), digital versatile disk drive(s), etc. While in the illustrated example the badges data store 1225 is illustrated as a single database, the badges data store 1225 may be implemented by any number and/or type(s) of databases.

In the illustrated example of FIG. 12, the example RTLS server 455 includes the example asset-location engine 1230 to associate mobile-location assets with corresponding locations. In some examples, the locations determined by the asset-location engine 1230 may be used to track the location of the mobile-location asset through an environment 400 of FIG. 4 such as a hospital. For example, by comparing the location of a mobile-location asset (e.g., a wheelchair) over two or more intervals, the example RTLS server 455 may determine whether the mobile-location asset is moving (e.g., the current location is different than a previously-associated location) or is stationary (e.g., the current location is the same location as a previously-associated location). In the illustrated example of FIG. 12, the asset-location engine 1230 includes an example tag-type filterer 1235, an example location classifier 1240 and an example location handler 1245.

The example asset-location engine 1230 of FIG. 12 includes the tag-type filterer 1235 to process the messages logged in the messages data store 1207 and identify the reader messages 430 associated with mobile-location assets. For example, the tag-type filterer 1235 may parse the tag-type identifying information 420 included in the reader messages 430 to identify the mobile-location asset reader messages. In some examples, the tag-type filterer 1235 may log the identified mobile-location asset reader messages in the assets data store 1250.

The example asset-location engine 1230 of FIG. 12 includes the location classifier 1240 to classify the location of the beacon tags corresponding to the mobile-location asset reader messages relative to the location of the reader badge 425. For example, the location classifier 1240 may classify the locations of the beacon tags relative to the location of the reader badge 425 based on signal strength (e.g., the signal strength information 445 included in the corresponding reader message 430). In the illustrated example of FIG. 12, the location classifier 1240 classifies a beacon tag as relatively-far from the reader badge 425 when the signal strength included in the corresponding reader message 430 is low (e.g., the RSSI value is less than (−60) decibels). The example location classifier 1240 classifies a beacon tag as relatively-immediate to the reader badge 425 when the signal strength included in the corresponding reader message 430 is high (e.g., the RSSI value is greater than (−40) decibels). The example location classifier 1240 classifies a beacon tag as relatively-near to the reader badge 425 when the signal strength included in the corresponding reader message 430 is medium (e.g., the RSSI value is greater than (−60) decibels and less than (−40) decibels).

In some examples, the location classifier 1240 may classify the location of the beacon tags based on the channel identifying information 450 included in the reader message 430. For example, beacon messages broadcast over a first channel may exhibit high variance in their signal strengths (e.g., a ten decibel range), beacon messages broadcast over a second channel may exhibit low variance in their signal strengths (e.g., a four decibel range), and beacon messages broadcast over a third channel may be susceptible to "bounce" events (e.g., beacon messages that are indirectly received by the reader badge 425 such as beacon messages 430 that bounce off of walls). In some such examples, the example location classifier 1240 may weight signal strength information and/or determined proximity relative to the reader badge based on their corresponding channel information. For example, if two beacon messages associated with the same signal strength are collected at the reader badge 425, but the first beacon message was broadcast over the second channel (e.g., associated with low variance) and the second beacon message was broadcast over the third channel (e.g., associated with "bounce" events), the example location classifier 1240 may determine that the first beacon message is relatively more reliable than the second beacon message in determining the proximity.

The example asset-location engine 1230 of FIG. 12 includes the location handler 1245 to determine a location of the mobile-location assets based on their location classifications. The example location handler 1245 of FIG. 12 also manages confidence scores associated with the mobile-location assets. In some examples, the asset-location confidence scores may represent a likelihood that a mobile-location asset is at its current location. The example location handler 1245 of FIG. 12 stores the determined mobile-location asset-location mappings and their corresponding confidence scores in the example assets data store 1250.

In the illustrated example of FIG. 12, when an asset-location is relatively-far from the reader badge 425, the example location handler 1245 does not update the location of the asset. The example location handler 1245 also makes no change to the confidence score associated with the asset and its current location mapping.

In the illustrated example of FIG. 12, when an asset-location is relatively-immediate to the reader badge 425, the example location handler 1245 updates the location of the asset to the location of the reader badge 425. For example, the location handler 1245 may retrieve the corresponding reader badge-location mapping from the badges data store 1225 and update the corresponding mobile-location asset-location mapping in the assets data store 1250. The example location handler 1245 also increments the asset-location confidence score of the corresponding mobile-location asset-location mapping in the assets data store 1250. In some examples, the location handler 1245 may determine whether the current asset-location confidence score satisfies a maximum score threshold (e.g., the current asset-location confidence score is less than the maximum score threshold). If the current asset-location confidence score does not satisfy the maximum score threshold (e.g., the current asset-location score is equal to the maximum score threshold), the location handler 1245 may not increment the current asset-location confidence score.

In the illustrated example of FIG. 12, when an asset-location is relatively-near to the reader badge 425, the example location handler 1245 compares the current asset-location to the location of the reader badge 425. For example, the location handler 1245 may retrieve the corresponding reader badge-location mapping from the badges data store 1225 and compare the reader badge location to the current asset-location retrieved from the assets data store 1250. In the illustrated example, when the reader badge-location and the current asset-location are the same, the example location handler 1245 increments the asset-location confidence score of the corresponding mobile-location asset-location mapping in the assets data store 1250. However, when the current asset-location confidence score does not satisfy the maximum score threshold (e.g., the current asset-location score is equal to the maximum score threshold), the location handler 1245 may not increment the current asset-location confidence score.

In some examples when the asset-location is relatively-near to the reader badge 425 but the reader badge-location and the current asset-location are not the same, the example location handler 1245 decrements the location confidence score of the corresponding mobile-location asset-location mapping in the assets data store 1250. In some examples, the location handler 1245 may determine whether the updated asset-location confidence score satisfies a minimum score threshold (e.g., the current asset-location confidence score is greater than the minimum score threshold). In the illustrated example, when the current asset-location confidence score does not satisfy the minimum score threshold (e.g., the current asset-location score is equal to the minimum score threshold), the location handler 1245 updates the location of the asset to the location of the reader badge 425. For example, the location handler 1245 may retrieve the corresponding reader badge-location mapping from the badges data store 1225 and update the corresponding mobile-location asset-location mapping in the assets data store 1250. The example location handler 1245 also resets the asset-location confidence score of the corresponding mobile-location asset-location mapping in the assets data store 1250. For example, the location handler 1245 may set the asset-location confidence score to one.

In the illustrated example, the asset-location engine 1230 stores the determined mobile-location asset-location mappings in the example assets data store 1250 of FIG. 12. An example data table 1500 representing mobile-location assets and their associated location mappings is shown in FIG. 15. The example assets data store 1250 may be implemented by a volatile memory (e.g., a Synchronous Dynamic Random Access Memory (SDRAM), Dynamic Random Access Memory (DRAM), RAMBUS Dynamic Random Access Memory (RDRAM), etc.) and/or a non-volatile memory (e.g., a flash memory). The example assets data store 1250 may additionally or alternatively be implemented by one or more double data rate (DDR) memories such as DDR, DDR2, DDR3, mobile DDR (mDDR), etc. The example assets data store 1250 may additionally or alternatively be implemented by one or more mass storage devices such as hard disk drive(s), compact disk drive(s), digital versatile disk drive(s), etc. While in the illustrated example the assets data store 1250 is illustrated as a single database, the assets data store 1250 may be implemented by any number and/or type(s) of databases.

In the illustrated example of FIG. 12, the example report generator 1255 generates reports based on information included in the example messages data store 1207, the example badges data store 1225 and/or the example assets data store 1250. The reports may identify different aspects of proximity detection and/or location tracking of assets in the example environment. For example, the report generator 1255 may generate a report identifying the current locations of one or more reader badges and/or mobile-location assets in the environment. In some examples, the report generator 1255 may generate a report identifying mobile-location assets that are proximate to a reader badge. For example, the report generator 1255 may retrieve the reader badge location information from the badges data store 1255 and query the assets data store for fixed-location assets with a matching location. In some examples, the report generator 1255 may generate a report tracking a location of a mobile-location asset through the example environment. For example, the report generator 1255 may retrieve the mobile-location asset-location mappings for the mobile-location asset over different timestamp intervals from the assets data store 1250. In some such examples, the report generator 1255 may also include a map of the environment that tracks the movement of the mobile-location asset.

In some examples, the example report generator 1255 of FIG. 12 may generate reports identifying adherence to procedures. For example, a hospital procedure may state that doctors are required to wash their hands when they enter a patient room. In some such instances, the example report generator 1255 may identify one or more reader badge(s) that were assigned to a doctor and track the movement of the doctor through the environment, and, more particularly, through patient rooms while they are visiting patients. However, the report generator 1255 of FIG. 12 may generate additional or alternative reports.

FIG. 13 illustrates an example data table 1300 that may be stored by the example messages data store 1207 of FIG. 12 to store reader messages 430 received from the reader beacon 425. For example, the example message message(s) receiver 1205 of FIG. 12 may log the one or more reader message(s) 430 when received.

The example data table 1300 includes an example reader identifier column 1305, an example tag identifier column 1310, an example tag-type identifier column 1315, an example timestamp column 1320, an example RSSI value identifying column 1325 and an example channel number identifying column 1330. The example reader identifier column 1305 indicates the reader badge that transmitted the one or more reader message(s) to the RTLS server 455. The example tag identifier column 1310 indicates the beacon tag 405 that broadcast the corresponding reader message 430. The example tag-type identifier column 1315 indicates the tag-type of the beacon tag. For example, the tag-type identifier column 1315 may indicate whether the beacon tag is affixed to a fixed-location asset or to a mobile-location asset. The example timestamp column 1320 indicates when (e.g., a date and/or time) when the corresponding beacon message 410 was received. The example RSSI value identifying column 1325 indicates the signal strength (e.g., power level) of the received beacon message 410. The example channel number identifying column 1330 indicates a channel on which the beacon message 410 was received (e.g., a Bluetooth frequency channel such as channel 37, channel 38 or channel 39). However, any other columns representing any other conditions and/or characteristics of the access request may additionally or alternatively be used. Moreover, the example column(s) of the example data table 800 may be implemented in any other fashion (e.g., using a different data structure).

The example data table 1300 of the illustrated example of FIG. 13 includes three example rows 1350, 1355, 1360 corresponding to three different reader messages received by the RTLS server 455. The example first row 1350 indicates that a "Reader 1" reader badge received a beacon message from a beacon tag ("Entry_1") that is affixed to a "fixed-location asset" at "0:00:01." In addition, the signal strength of the beacon message corresponding the example first row 1350 was "high" (e.g., was greater than or equal to (−40) decibels) and was received on channel number "37."

The example second row 1355 indicates that a "Reader 1" reader badge received a beacon message from a beacon tag ("Chair_1") that is affixed to a "mobile-location asset" at "0:00:02." In addition, the signal strength of the beacon message corresponding the example second row 1355 was "low" (e.g., was less than or equal to (−60) decibels) and was received on channel number "37."

The example third row 1360 indicates that a "Reader_1" reader badge received a second beacon message from the beacon tag ("Chair_1") that is affixed to a "mobile-location asset" at "0:00:03." In addition, the signal strength of the beacon message corresponding the example third row 1360 was "med" (e.g., was greater than (−60) decibels and less than (−40) decibels) and was received on channel number "38." While three example received reader messages are represented in the example data table 1300 of FIG. 13, more or fewer reader messages may be received at the RTLS server 455.

FIG. 14 illustrates an example data table 1400 that may be stored by the example badges data store 1225 of FIG. 12 to store reader badge-location mappings. For example, the example badge location engine 1210 of FIG. 12 may log the reader badge and the associated location during particular intervals in the badges data store 1225.

The example data table 1400 includes an example reader identifier column 1405, an example tag identifier column 1410, an example timestamp interval column 1415 and an example reader badge location identifying column 1420. The example reader identifier column 1405 indicates a reader badge for which a location mapping is determined. The example tag identifier column 1410 indicates the nearest beacon tag 405 to the reader badge 425. For example, tag identifier column 1410 may identify the fixed-location asset beacon tag that broadcast a beacon message that was collected by the corresponding reader badge with the strongest signal strength. The example timestamp interval column 1415 indicates an interval of time during which the reader badge-location mapping is applicable. For example, reader badge-location mappings may be prepared for a reader badge across different time periods. The example reader badge location identifying column 1420 indicates the location associated with the reader badge during the corresponding timestamp interval. However, any other columns representing any other conditions and/or characteristics of the access request may additionally or alternatively be used. Moreover, the example column(s) of the example data table 1400 may be implemented in any other fashion (e.g., using a different data structure).

The example data table 1400 of the illustrated example of FIG. 14 includes three example rows 1450, 1455, 1460 corresponding to three different reader badge-location mappings determined by the RTLS server 455. The example first row 1450 indicates that during a first timestamp interval ("0:00:00-0:00:05"), a "Reader 1" reader badge was determined to be located in entry #1 of a patient room #1. The location associated with the "Reader 1" reader badge during the first timestamp interval was determined by the proximity of the "Reader 1" reader badge to the "Entry_1" beacon tag.

The example second row 1455 indicates that during a second timestamp interval ("0:00:10-0:00:15"), the "Reader 1" reader badge was determined to be located at a water fountain #2 in hallway #12. The location associated with the "Reader 1" reader badge during the second timestamp interval was determined by the proximity of the "Reader 1" reader badge to the "water fountain 2" beacon tag.

The example third row 1460 indicates that during a third timestamp interval ("0:02:20-0:02:25"), the "Reader 1" reader badge was determined to be located at a sink #2 in patient room #1. The location associated with the "Reader 1" reader badge during the third timestamp interval was determined by the proximity of the "Reader 1" reader badge to the "sink 2" beacon tag. While three example reader badge-location mappings are represented in the example data table 1400 of FIG. 14, more or fewer reader badge-location mappings may be generated by the example RTLS server 455.

FIG. 15 illustrates an example data table 1500 that may be stored by the example assets data store 1250 of FIG. 12 to store mobile-location asset-location mappings. For example, the example asset-location engine 1230 of FIG. 12 may log the mobile-location asset beacon tag and the associated location during particular intervals in the assets data store 1250. In the illustrated example, the asset-location engine 1230 also records an asset-location confidence score associated with the current location of the mobile-location asset.

The example data table 1500 includes an example tag identifier column 1505, an example current location identifying column 1510, an example timestamp interval column 1415 and an example asset-location confidence score column 1520. The example tag identifier column 1505 indicates a beacon tag, and, as a result, a mobile-location asset, for which a location mapping is determined. The example current location identifying column 1510 indicates the current location associated with the corresponding mobile-location asset. The example timestamp interval column 1515 indicates an interval of time during which the mobile-location asset-location mapping is applicable. For example, mobile-location asset-location mappings may be prepared for mobile-location asset across different time periods. The example asset-location confidence score column 1520 indicates a confidence score associated with the current location of the corresponding mobile-location asset. However, any other columns representing any other conditions and/or characteristics of the access request may additionally or alternatively be used. Moreover, the example column(s) of the example data table 1500 may be implemented in any other fashion (e.g., using a different data structure).

The example data table 1500 of the illustrated example of FIG. 15 includes four example rows 1550, 1555, 1560, 1565 corresponding to four different mobile-location asset-location mappings determined by the RTLS server 455. The example first row 1550 indicates that during a first timestamp interval ("0:00:00-0:00:05"), a "Chair #2" mobile-location asset was determined to be located in entry #1 of a patient room #1. The example first row 1550 also indicates that the confidence score of the asset-location mapping is "37." In the illustrated example, if a subsequent reader message 430 indicates that the "Chair #2" mobile-location asset is relatively-near and/or relatively-immediate to a reader badge (e.g., the reader badge 425) assigned to the entry #1 of the patient room #1, the asset-location confidence score associated with the "Chair #2" being located in the entry #1 of the patient room #1 may be increased to "38." In other examples, if a subsequent reader message 430 indicates that the "Chair #2" mobile-location asset is relatively-far from the reader badge 425, the asset-location confidence score associated with the "Chair #2" being located in the entry #1 of the patient room #1 may be decreased to "36."

The example second row 1555 indicates that during the first timestamp interval ("0:00:00-0:00:05"), a "Chair #3" mobile-location asset was determined to be located in a closet #3 of a hallway #2. The example second row 1555 also indicates that the confidence score of the asset-location mapping is "1." In the illustrated example, if a subsequent reader message 430 indicates that the "Chair #3" mobile-location asset is relatively-near and/or relatively-immediate to a reader badge (e.g., the reader badge 425) assigned to the closet #3 of the hallway #2, the asset-location confidence score associated with the "Chair #3" being located in the closet #3 of the hallway #2 may be increased to "2." In other examples, if a subsequent reader message 430 indicates that the "Chair #3" mobile-location asset is relatively-far from the reader badge 425, the asset-location confidence score associated with the "Chair #3" being located in the closet #3 of the hallway #2 may be decreased to "0." In some such examples, the asset-location engine 1230 may determine that the updated asset-location confidence score ("0") is less than a minimum score threshold (e.g., "1") and update the current location information of the "Chair #3" mobile-location asset during the first timestamp interval to a current location assigned to a reader badge 425 that transmitted the corresponding reader message 430.

The example third row 1560 indicates that during a second timestamp interval ("0:02:00-0:02:05"), a "Walking Cane #12" mobile-location asset was determined to be located at sink #2 of a patient room #2. The example third row 1560 also indicates that the confidence score of the asset-location mapping is "50." In the illustrated example, if a subsequent reader message 430 indicates that the "Walking Cane #12" mobile-location asset is relatively-near and/or relatively-immediate to a reader badge (e.g., the reader badge 425) assigned to the sink #3 of the patient room #2, the asset-location confidence score associated with the "Walking Cane #12" being located at the sink #3 of the patient room #2 may be increased to "51." In some such examples, the asset-location engine 1230 may determine whether the current asset-location confidence score ("50") satisfies a maximum score threshold (e.g., "50") and, if so, not increment the asset-location confidence score. In other examples, if a subsequent reader message 430 indicates that the "Walking Cane #12" mobile-location asset is relatively-far from the reader badge 425, the asset-location confidence score associated with the "Walking Cane #12" being located at the sink #2 of the patient room #2 may be decreased to "49."

The example fourth row 1565 indicates that during the second timestamp interval ("0:02:00-0:02:05"), the "Chair #2" mobile-location asset was determined to be located at a water fountain #2 of a hallway #12. The example fourth row 1560 also indicates that the confidence score of the asset-location mapping is "13." In the illustrated example, if a subsequent reader message 430 indicates that the "Chair #2" mobile-location asset is relatively-near and/or relatively-immediate to a reader badge (e.g., the reader badge 425) assigned to the water fountain #2 of hallway #12, the asset-location confidence score associated with the "Chair #2" being located at the water fountain #2 of hallway #12 may be increased to "14." In other examples, if a subsequent reader message 430 indicates that the "Chair #2" mobile-location asset is relatively-far from the reader badge 425, the asset-location confidence score associated with the "Chair #2" being located at the water fountain #2 of hallway #12 may be decreased to "12."

While four example received mobile-location asset-location mappings and corresponding asset-location confidence scores are represented in the example data table 1500 of FIG. 15, more or fewer mobile-location asset-location mappings and corresponding asset-location confidence scores may be generated by the example RTLS server 455.

While an example implementation of the RTLS server 455 of FIG. 4 is illustrated in FIG. 12, one or more of the elements, processes and/or devices illustrated in FIG. 12 may be combined, divided, re-arranged, omitted, eliminated and/or implemented in any other way. Further, the example message(s) receiver 1205, the example messages data store 1207, the example badge location engine 1210, the example tag-type filterer 1215, the example distance determiner 1220, the example badges data store 1225, the example asset-location engine 1230, the example tag-type filterer 1235, the example location classifier 1240, the example location handler 1245, the example report generator 1255 and/or, more generally, the example RTLS server 455 of FIG. 4 may be implemented by hardware, software, firmware and/or any combination of hardware, software and/or firmware. Thus, for example, any of the example message(s) receiver 1205, the example messages data store 1207, the example badge location engine 1210, the example tag-type filterer 1215, the example distance determiner 1220, the example badges data store 1225, the example asset-location engine 1230, the example tag-type filterer 1235, the example location classifier 1240, the example location handler 1245, the example report generator 1255 and/or, more generally, the example RTLS server 455 of FIG. 4 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example message(s) receiver 1205, the example messages data store 1207, the example badge location engine 1210, the example tag-type filterer 1215, the example distance determiner 1220, the example badges data store 1225, the example asset-location engine 1230, the example tag-type filterer 1235, the example location classifier 1240, the example location handler 1245, the example report generator 1255 and/or, more generally, the example RTLS server 455 of FIG. 4 is/are hereby expressly defined to include a tangible computer readable storage device or storage disk such as a memory, a digital versatile disk (DVD), a compact disk (CD), a Blu-ray disk, etc. storing the software and/or firmware. Further still, the example RTLS server 455 of FIG. 4 may include one or more elements, processes and/or devices in addition to, or instead of, those illustrated in FIG. 12, and/or may include more than one of any or all of the illustrated elements, processes and devices.

Figure 16:
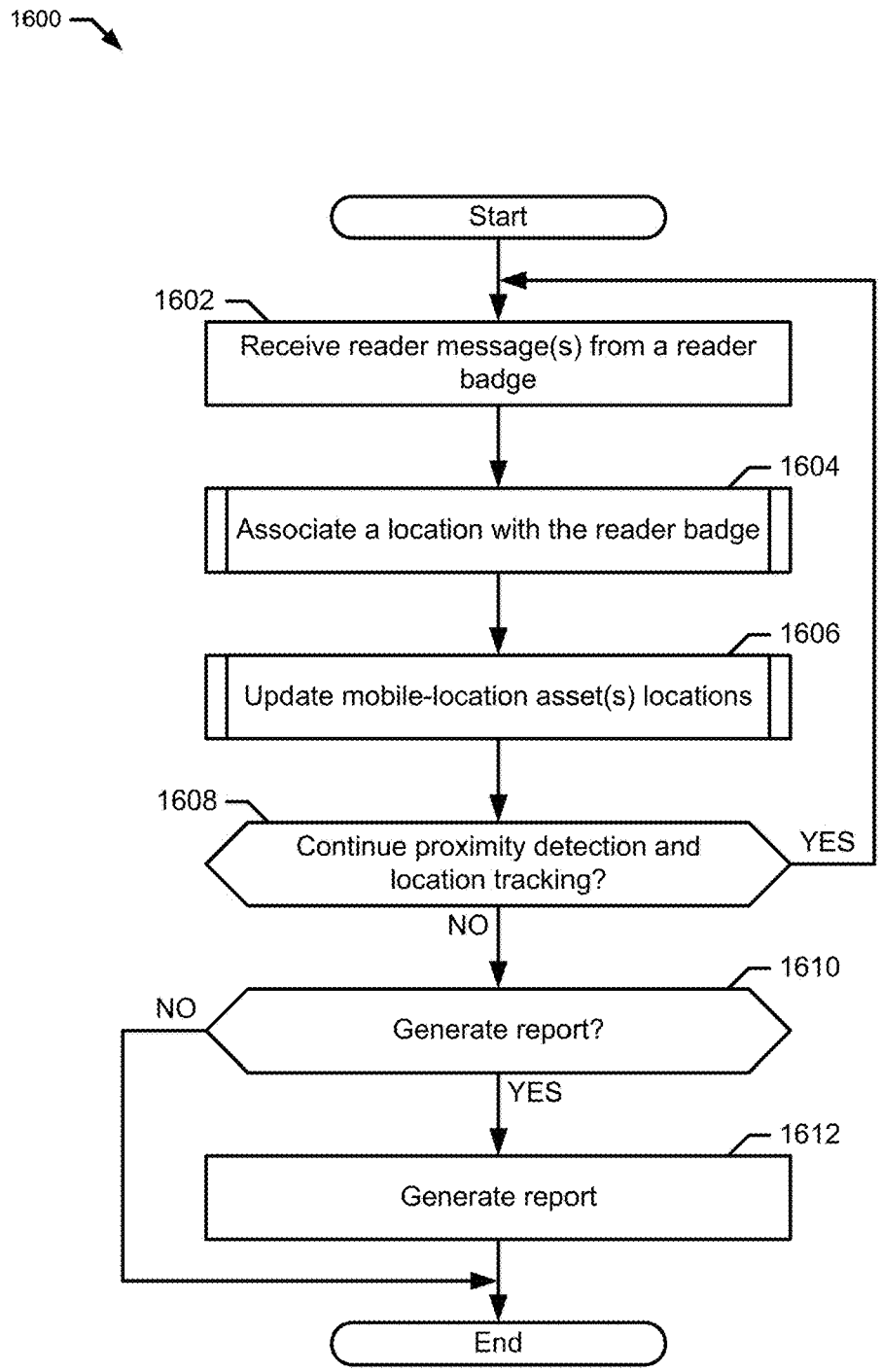
FIG. 16 is a flowchart representative of example machine-readable instructions that may be executed to facilitate proximity detection and location tracking in the environment of FIG. 4.
Figure 17:
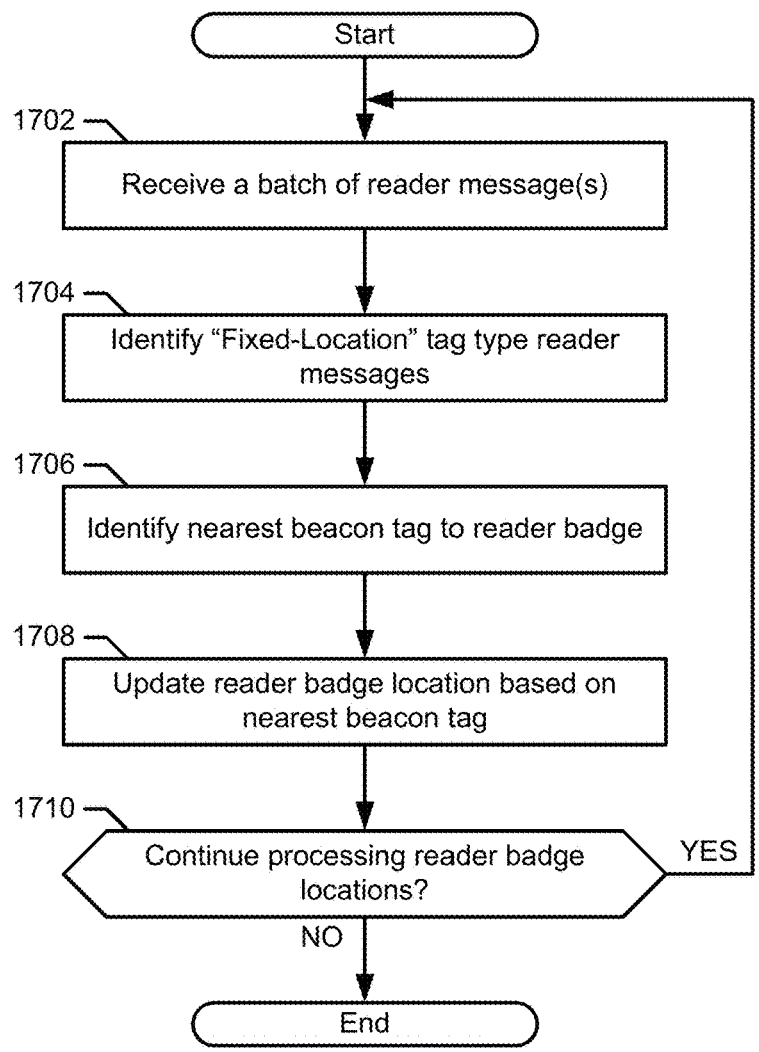
FIG. 17 is a flowchart representative of example machine-readable instructions that may be executed to generate a reader badge-location mapping in the environment of FIG. 4.
Figure 18:
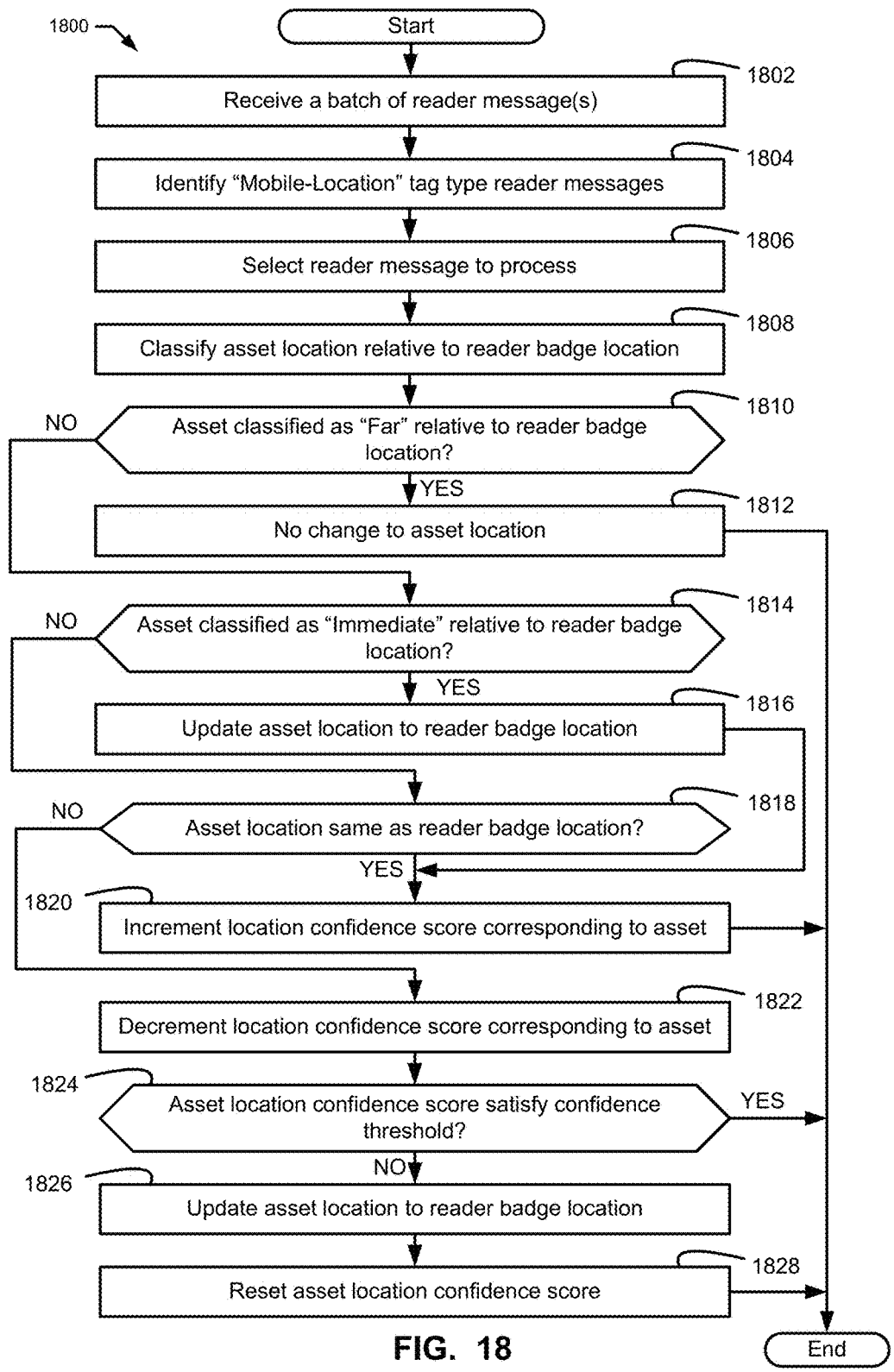
FIG. 18 is a flowchart representative of example machine-readable instructions that may be executed to "crowd-source" a location of an asset in the environment of FIG. 4.

Flowcharts representative of example machine-readable instructions for implementing the example RTLS server 455 of FIGS. 4 and/or 12 are shown in FIGS. 16-18. In these examples, the machine-readable instructions comprise a program(s) for execution by a processor such as the processor 1912 shown in the example processor platform 1900 discussed below in connection with FIG. 19. The program(s) may be embodied in software stored on a tangible computer readable storage medium such as a CD-ROM, a floppy disk, a hard drive, a digital versatile disk (DVD), a Blu-ray disk, or a memory associated with the processor 1912, but the entire program(s) and/or parts thereof could alternatively be executed by a device other than the processor 1912 and/or embodied in firmware or dedicated hardware. Further, although the example program(s) is/are described with reference to the flowchart illustrated in FIGS. 16, 17 and/or 18, many other methods of implementing the example RTLS server 455 of FIGS. 4 and/or 12 may alternatively be used. For example, the order of execution of the blocks may be changed, and/or some of the blocks described may be changed, eliminated, or combined.

As mentioned above, the example processes of FIGS. 16, 17 and/or 18 may be implemented using coded instructions (e.g., computer and/or machine-readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine-readable storage medium" are used interchangeably. Additionally or alternatively, the example processes of FIGS. 16, 17 and/or 18 may be implemented using coded instructions (e.g., computer and/or machine-readable instructions) stored on a non-transitory computer and/or machine-readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. Comprising and all other variants of "comprise" are expressly defined to be open-ended terms. Including and all other variants of "include" are also defined to be open-ended terms. In contrast, the term consisting and/or other forms of consist are defined to be close-ended terms.

FIG. 16 is a flowchart representative of example machine-readable instructions 1600 that may be executed to implement the example RTLS server 455 of FIGS. 4 and/or 12 to facilitate proximity detection and location tracking. The example instructions 1600 of the illustrated example of FIG. 16 begin at block 1602 when the example RTLS server 455 receives one or more reader message(s) 430 from a reader badge 425. For example, the message(s) receiver 1205 (FIG. 12) may receive one or more reader message(s) 430 via the example network 460 (FIG. 4). In some examples, the message(s) receiver 1205 records the received reader message(s) in the example messages data store 1207 (FIG. 12). At block 1604, the example RTLS server 455 associates a location with the reader badge. For example, the example badge location engine 1210 may determine a nearest fixed-location asset beacon tag to the reader badge 425 and assign the location of the fixed-location asset to the reader badge 425. At block 1606, the example RTLS server 455 updates locations of mobile-location asset(s). For example, the example asset-location engine 1230 (FIG. 12) may identify one or more mobile-location asset(s) relatively-near or relatively-immediate to the reader badge 425 and update the location of the mobile-location asset and/or update an asset-location confidence score associated with the current location of the mobile-location asset.

At block 1608, the example RTLS server 455 determines whether to continue proximity detection and location tracking. If, at block 1608, the example RTLS server 455 determined to continue proximity detection and location tracking, then control returns to block 1602 to receive one or more reader message(s) from a reader badge.

If, at block 1608, the example RTLS server 455 determined not to continue proximity detection and location tracking, then, at block 1610, the example RTLS server 455 determines whether to generate a report. For example, the RTLS server 455 may receive a request to generate a report regarding one or more reader badge(s), one or more mobile-location asset(s) and/or adherence of one or more healthcare worker(s) to procedure(s) of the hospital. If, at block 1610, the RTLS server 455 determined to generate a report, then, at block 1612, the example report generator 1255 (FIG. 12) generates a report. For example, the report generator 1255 may generate a report based on conditions of a request to generate a report (e.g., based on one or more reader badge(s), one or more mobile-location asset(s) and/or adherence of one or more healthcare worker(s) to procedure(s) of the hospital).

If, at block 1610, the example RTLS server 455 determined not to generate a report, or, after the example report generator 1255 generated a report at block 1612, then the example program 1600 of FIG. 16 ends.

FIG. 17 is a flowchart representative of example machine-readable instructions 1700 that may be executed to implement the example RTLS server 455 of FIGS. 4 and/or 12 to assign a location to a reader badge. The example method 1700 may be used to implement block 1604 of FIG. 16. The example instructions 1700 of the illustrated example of FIG. 17 begin at block 1702 when the example badge location engine 1210 (FIG. 12) receives a batch (e.g., one or more) reader message(s) 430. For example, the badge location engine 1210 may retrieve one or more reader message(s) 430 from the example messages data store 1207 that are associated with a timestamp interval and that were received at a same reader badge 425. At block 1704, the example badge location engine 1210 (FIG. 12) identifies one or more reader message(s) 430 that are of "fixed-location" tag type. For example, the example tag-type filterer 1215 (FIG. 12) may parse the tag-type identifying information 420 included in the reader messages 430 to identify the fixed-location asset reader messages.

At block 1706, the example badge location engine 1210 identifies a nearest beacon tag to the reader badge. For example, the example distance determiner 1220 (FIG. 12) may parse the fixed-location tag-type reader message(s) for the strongest signal strength. The example distance determiner 1220 may associate the beacon tag 405 corresponding to the strongest signal strength as the nearest beacon tag to the reader badge. At block 1708, the example badge location engine 1210 updates the location assigned to the reader badge based on the nearest beacon tag. For example, the distance determiner 1220 may update a reader badge-location mapping in the badges data store 1225 during the timestamp interval to the fixed-location associated with the nearest beacon tag. At block 1710, the example badge location engine 1210 determines whether to continue processing reader badge locations. If, at block 1710, the example badge location engine 1210 determined to continue processing reader badge locations (e.g., the messages data store 1207 includes unprocessed reader message(s)), then control returns to block 1702 to receive a batch of reader message(s). If, at block 1710, the example badge location engine 1210 determined not to continue processing reader badge locations, the example program 1700 of FIG. 17 ends.

FIG. 18 is a flowchart representative of example machine-readable instructions 1800 that may be executed to implement the example RTLS server 455 of FIGS. 4 and/or 12 to assign a location to mobile-location assets. For example, the example instructions 1800 of the illustrated example may be executed to "crowd-source" a location of an asset based on, for example, an asset location confidence score. The example method 1800 may be used to implement block 1606 of FIG. 16. The example instructions 1800 of the illustrated example of FIG. 18 begin at block 1802 when the example asset-location engine 1230 (FIG. 12) receives a batch (e.g., one or more) reader message(s) 430. For example, the asset-location engine 1230 may retrieve one or more reader message(s) 430 from the example messages data store 1207 that are associated with a timestamp interval and that were received at a same reader badge 425. At block 1804, the example asset-location engine 1230 identifies one or more reader message(s) 430 that are of "mobile-location" tag type.

For example, the example tag-type filterer 1235 (FIG. 12) may parse the tag-type identifying information 420 included in the reader messages 430 to identify the mobile-location asset reader messages. At block 1806, the example asset-location engine 1230 selects a reader message and the corresponding mobile-location asset to process.

At block 1808, the example asset-location engine 1230 classifies a location of the corresponding mobile-location asset relative to the location of the reader badge 425 that received the reader message 430. For example, the example location classifier 1240 (FIG. 12) may classify a mobile-location asset as relatively-far from the reader badge 425 when the signal strength associated with the selected reader message 430 is low (e.g., is less than or equal to (−60) decibels), may classify a mobile-location asset as relatively-immediate to the reader badge 425 when the signal strength associated with the selected reader message 430 is high (e.g., is greater than or equal to (−40) decibels), and may classify a mobile-location asset as relatively-near to the reader badge 425 when the signal strength associated with the selected reader message 430 is medium (e.g., is greater than (−60) decibels and less than (−40) decibels). However, other ranges may additionally or alternatively be used.

At block 1810, the example asset-location engine 1230 determines whether the asset-location is classified as relatively-far to the reader badge 425 (e.g., the signal strength is less than or equal to (−60) decibels). If, at block 1810, the example asset-location engine 1230 determined that the asset-location is classified as relatively-far, then, at block 1812, no change is made to the asset-location and no change is made to the corresponding asset-location confidence score. The example program 1800 of FIG. 18 then ends.

If, at block 1810, the example asset-location engine 1230 determined that the asset-location is not classified as relatively-far, then, at block 1814, the example asset-location engine 1230 determines whether the asset-location is classified as relatively-immediate to the reader badge 425 (e.g., the signal strength is greater than or equal to (−40) decibels). If, at block 1814, the example asset-location engine 1230 determined that the asset-location is classified as relatively-immediate, then, at block 1816, the example asset-location engine 1230 updates the asset-location to the reader badge location. For example, the example location handler 1245 (FIG. 12) may retrieve the corresponding reader badge-location mapping from the badges data store 1225 and update the mobile-location asset-location mapping in the assets data store 1250 accordingly. Control then proceeds to block 1820 to increment the location confidence score corresponding to the asset. In some examples, the location handler 1245 may not increment the location confidence score if, for example, the current asset-location confidence score satisfies a maximum score threshold. The example program 1800 of FIG. 18 then ends.

If, at block 1814, the example asset-location engine 1230 determined that the asset-location is not classified as relatively-immediate, then, at block 1818, the example asset-location engine 1230 determines whether the current location associated with the mobile-location asset is the same as the location assigned to the reader badge 425. If, at block 1818, the example asset-location engine 1230 determined that the current location associated with the mobile-location asset is the same as the location assigned to the reader badge 425, then, at block 1820, the example location handler 1245 increments the location confidence score corresponding to the asset. In some examples, the location handler 1245 may not increment the location confidence score if, for example, the current asset-location confidence score satisfies a maximum score threshold. The example program 1800 of FIG. 18 then ends.

If, at block 1818, the example asset-location engine 1230 determined that the current location associated with the mobile-location asset is not the same as the location assigned to the reader badge 425, then, at block 1822, the example asset-location engine 1230 decrements the location confidence score corresponding to the asset. For example, the location handler 1245 may decrement the corresponding asset-location confidence score in the assets data store 1250. At block 1824, the example asset-location engine 1230 determines whether the updated asset-location confidence score satisfies a confidence threshold. For example, the location handler 1245 may determine whether the updated asset-location confidence score is greater than or equal to a minimum score (e.g., one). If, at block 1824, the asset-location engine 1230 determined that the updated asset-location confidence score is greater than or equal to the minimum score (e.g., one), the example program 1800 of FIG. 18 ends.

If, at block 1824, the asset-location engine 1230 determined that the updated asset-location confidence score is not greater than or equal to the minimum score (e.g., the updated asset-location confidence score is zero), then, at block 1826, the example asset-location engine 1230 updates the asset-location to the location of the reader badge 425. For example, the location handler 1245 may retrieve the corresponding reader badge-location mapping from the badges data store 1225 and update the location of the asset accordingly. At block 1828, the example asset-location engine 1230 resets the asset-location confidence score. For example, the location handler 1245 may set the asset-location confidence score to one. The example program 1800 of FIG. 18 then ends.

Figure 19:
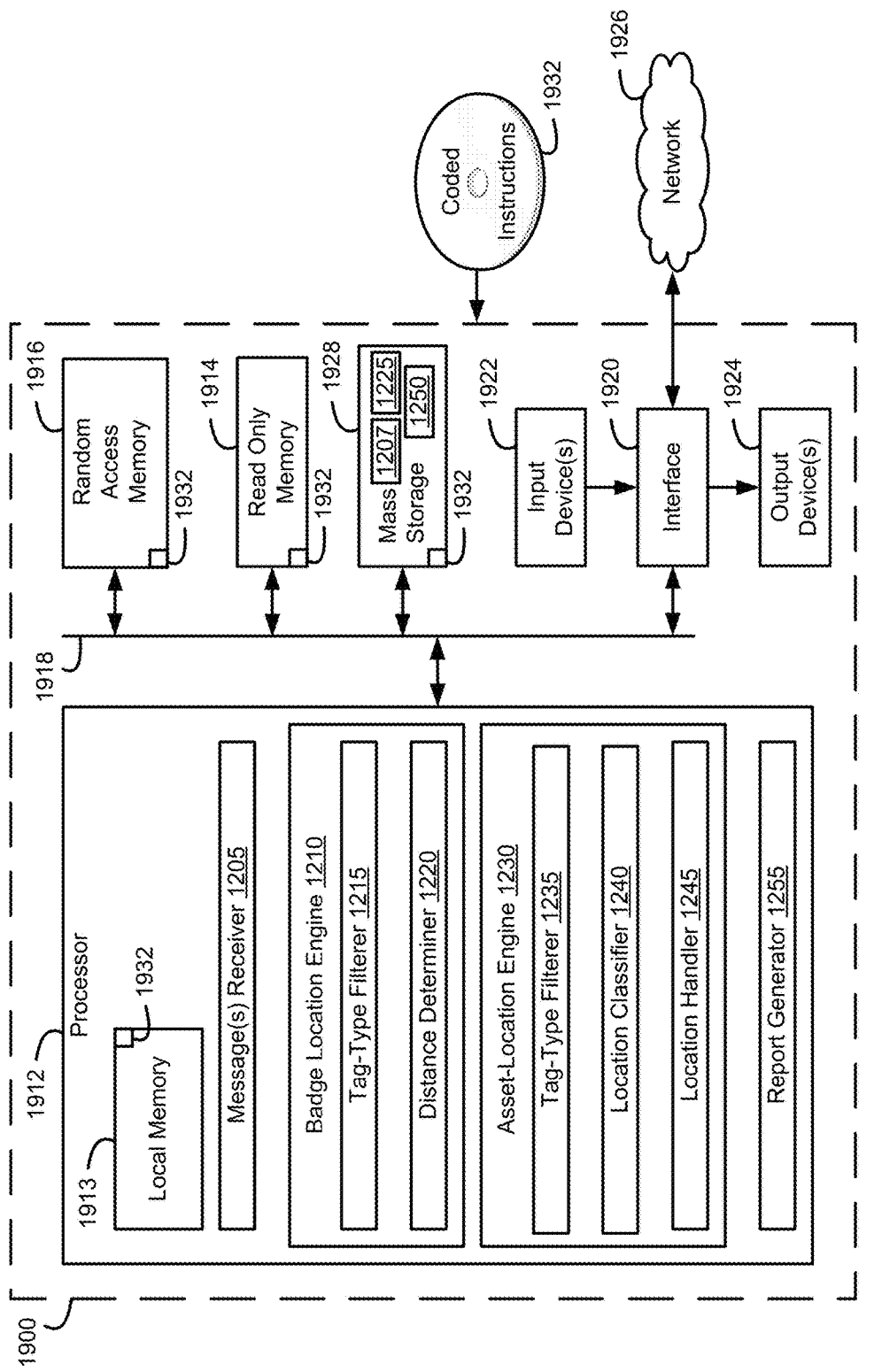
FIG. 19 is a block diagram of an example server structured to execute the example machine-readable instructions of FIGS. 16, 17 and/or 18 to implement the example RTLS server of FIG. 4.

FIG. 19 is a block diagram of an example processor platform 1900 capable of executing the instructions of FIGS. 16, 17 and/or 18 to implement the example RTLS server 455 of FIGS. 4 and/or 12. The processor platform 1900 can be, for example, a server, a personal computer, or any other type of computing device.

The processor platform 190 of the illustrated example includes a processor 1912. The processor 1912 of the illustrated example is hardware. For example, the processor 1912 can be implemented by one or more integrated circuits, logic circuits, microprocessors or controllers from any desired family or manufacturer.

The processor 1912 of the illustrated example includes a local memory 1913 (e.g., a cache). The processor 1912 of the illustrated example executes the instructions to implement the example message(s) receiver 1205, the example messages data store 1207, the example badge location engine 1210, the example tag-type filterer 1215, the example distance determiner 1220, the example badges data store 1225, the example asset-location engine 1230, the example tag-type filterer 1235, the example location classifier 1240, the example location handler 1245, the example report generator 1255 and/or, more generally, the example RTLS server 455 of FIGS. 4 and/or 5. The processor 1912 of the illustrated example is in communication with a main memory including a volatile memory 1914 and a non-volatile memory 1916 via a bus 1918. The volatile memory 1914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1916 may be implemented by flash memory and/or any other desired type of memory device. Access to the main memory 1914, 1916 is controlled by a memory controller.

The processor platform 1900 of the illustrated example also includes an interface circuit 1920. The interface circuit 1920 may be implemented by any type of interface standard, such as an Ethernet interface, a universal serial bus (USB), and/or a PCI express interface.

In the illustrated example, one or more input devices 1922 are connected to the interface circuit 1920. The input device(s) 1922 permit(s) a user to enter data and commands into the processor 1912. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1924 are also connected to the interface circuit 1920 of the illustrated example. The output devices 1924 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1920 of the illustrated example, thus, typically includes a graphics driver card, a graphics driver chip or a graphics driver processor.

The interface circuit 1920 of the illustrated example also includes a communication device such as a transmitter, a receiver, a transceiver, a modem and/or network interface card to facilitate exchange of data with external machines (e.g., computing devices of any kind) via a network 1926 (e.g., an Ethernet connection, a digital subscriber line (DSL), a telephone line, coaxial cable, a cellular telephone system, etc.).

The processor platform 1900 of the illustrated example also includes one or more mass storage devices 1928 for storing software and/or data. Examples of such mass storage devices 1928 include floppy disk drives, hard drive disks, compact disk drives, Blu-ray disk drives, RAID systems, and digital versatile disk (DVD) drives. The example mass storage 1928 implements the example messages data store 1207, the example badges data store 1225 and the example assets data store 1250.

The coded instructions 1932 of FIGS. 16, 17 and/or 18 may be stored in the mass storage device 1928, in the volatile memory 1914, in the non-volatile memory 1916, and/or on a removable tangible computer readable storage medium such as a CD or DVD.

Figure 20:
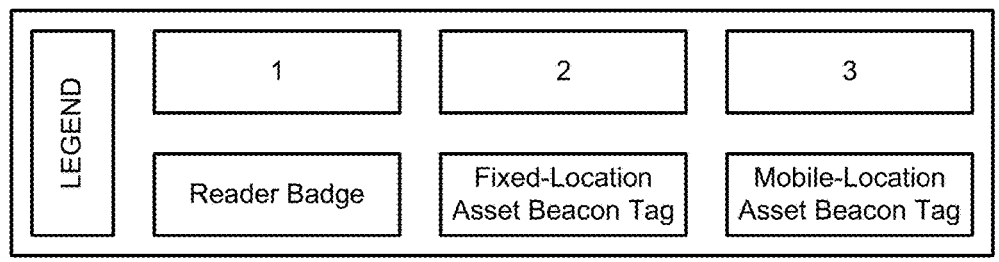
FIG. 20 illustrates an example environment to facilitate proximity detection and location tracking, according to the present disclosure.
Figure 20:
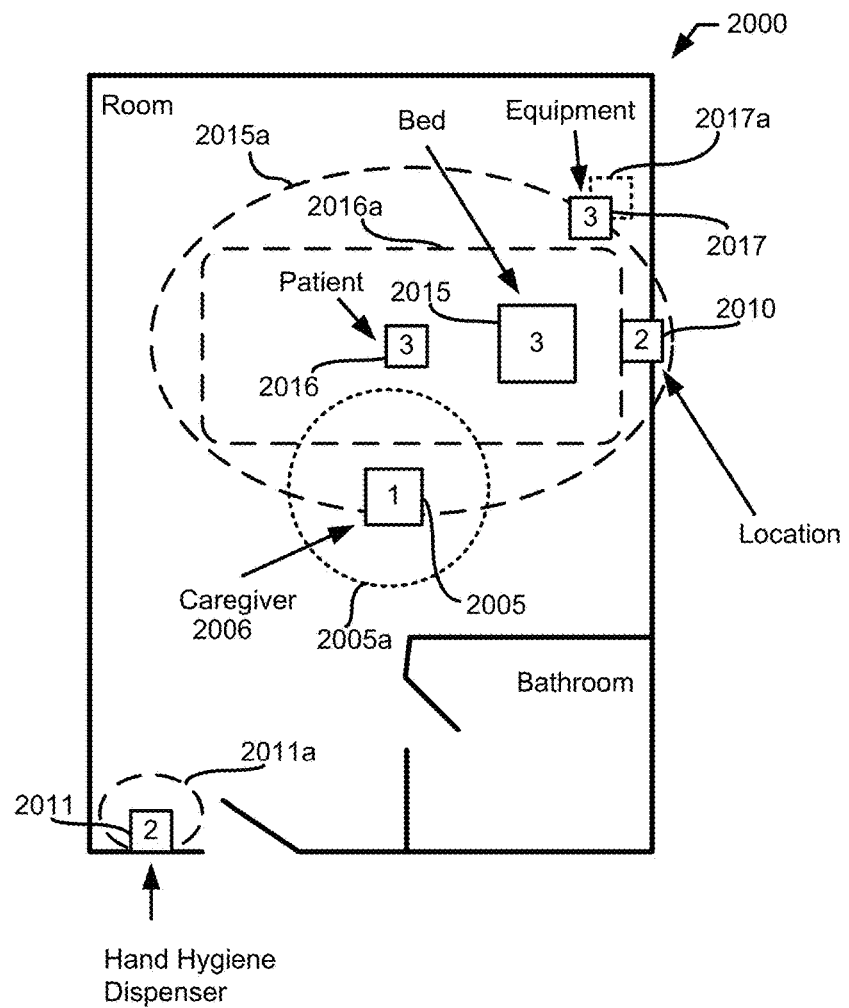

FIGS. 20-23 are illustrative example environments in which the example methods and apparatus to facilitate proximity detection and location tracking may be implemented. FIG. 20 illustrates an example patient room 2000 including an example reader badge 2005, example fixed-location asset beacon tags 2010, 2011 and example mobile-location asset beacon tags 2015-2017. In the illustrated example of FIG. 20, an example hospital caregiver 2006 is carrying the example reader badge 2005. The example fixed-location asset beacon tag 2010 is affixed to a headboard in the example patient room 2000. The example fixed-location asset beacon tag 2011 is affixed to a hand hygiene dispenser in the example patient room 2000. The example mobile-location asset beacon tag 2015 is affixed to a bed, the example mobile-location asset beacon tag 2016 is affixed to a patient (e.g., affixed to a patient ID band), and the example mobile-location asset beacon tag 2017 is affixed to equipment such as a wheelchair.

In the illustrated example of FIG. 20, the beacon tags 2011, 2015, 2016, 2017 are associated with broadcasting areas within which beacon messages broadcast by the respective beacon tags may be received (e.g., collected by the example reader badge 2005). For example, the first beacon tag 2011 broadcasts beacon messages within an example first broadcast area 2011a, the example second beacon tag 2015 broadcasts beacon messages within an example second broadcast area 2015a, the example third beacon tag 2016 broadcast beacon messages within an example third broadcast area 2016a and the example fourth beacon tag 2017 broadcasts beacon messages within an example fourth broadcast area 2017a. In addition, the example reader badge 2005 of FIG. 20 is associated with a proximity area 2005a in which the reader badge 2005 may receive beacon messages. In some examples, the proximity area 2005a and the broadcast areas 2011a, 2015a, 2016a, 2017a represent relatively-near locations. For example, in the illustrated example of FIG. 20, the proximity area 2005a overlaps with the example second broadcast area 2015a and the example third broadcast area 2016a. In some such examples, beacon messages that are collected by the reader badge 2005 may be used to classify the corresponding beacon tags as relatively-near to the reader badge 2005.

In contrast, because the broadcast area 2011a and the proximity area 2005a do not overlap in the illustrated example of FIG. 20, the first beacon tag 2011 is not located near or immediate relative to the reader badge 2005. In some such examples, a beacon message that is received by the reader badge 2005 and that was broadcast by the first beacon tag 2011 would be determined to have low signal strength and, thus, classified as relatively-far from the reader badge 2005. In some examples, when the proximity area of a reader badge overlaps with a beacon tag, the beacon tag location is determined to be relatively-immediate to the reader badge.

As described above, the relatively-near and/or relatively-immediate classifications may be used to "crowd-source" the location of assets. In the illustrated example of FIG. 20, because the second and third beacon tags 2015, 2016 are classified as relatively-near the caregiver (e.g., the reader badge 2005), confidence that the corresponding assets (e.g., the bed and the patient, respectively) are in the same location is increased. In addition, subsequent relatively-near classifications, based on, for example, other reader badges as caregivers walk into and out of the patient room 2000, may further increase the confidence that the corresponding assets are located in the patient room 2000.

Additionally, user behavior may also be monitored based on the proximity detection and location tracking. For example, the proximity of the caregiver to the patient may indicate that the caregiver is interacting with the patient. In the illustrated example, because the proximity area 2005a does not overlap with the broadcast area 2011a associated with the hand hygiene dispenser, a determination may be made that the caregiver is not interacting with (e.g., using) the hand hygiene dispenser. Moreover, if analysis of previous timestamp intervals also does not show the proximity area 2005a overlapping with the broadcast area 2011a, a determination may be made that the caregiver did not use the hand hygiene dispenser prior to interacting with the patient.

Figure 21:
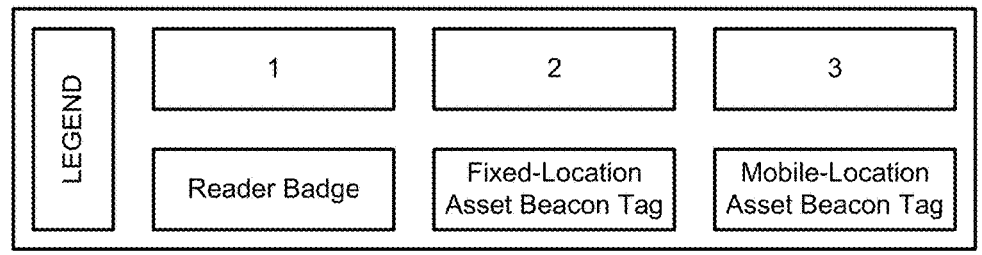
FIG. 21 illustrates another example environment to facilitate proximity detection and location tracking, according to the present disclosure.
Figure 21:
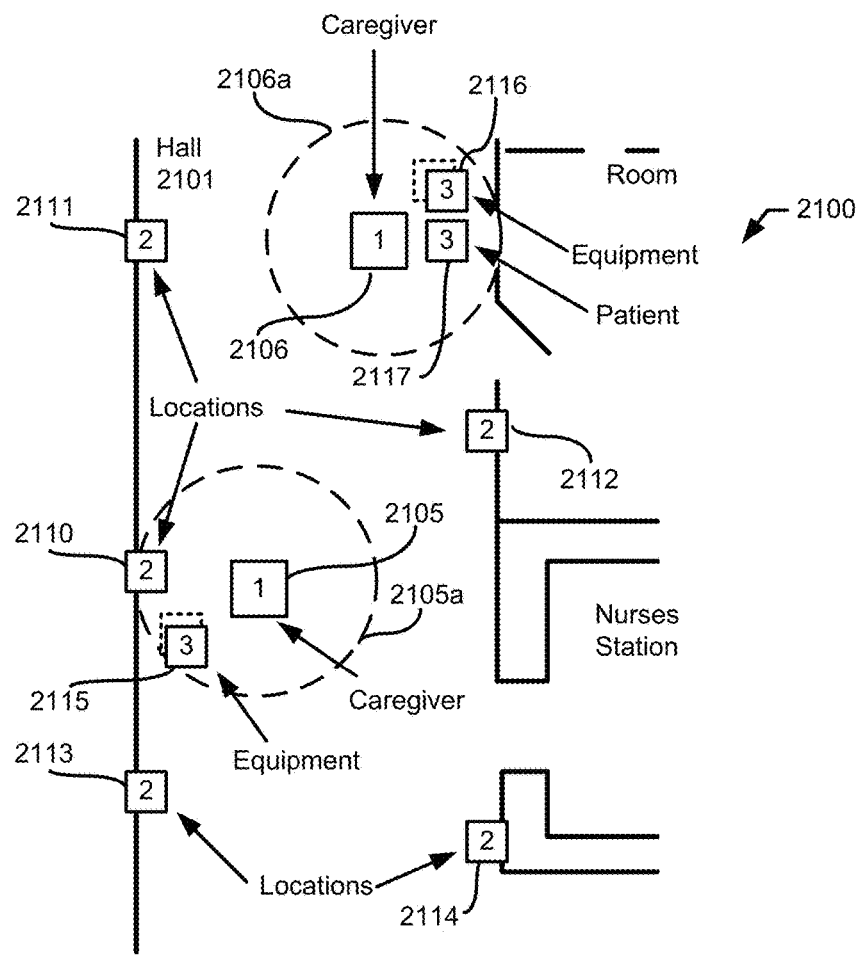

FIG. 21 illustrates an example environment 2100 including example reader badges 2105, 2106, example fixed-location asset beacon tags 2110-2114 and example mobile-location asset beacon tags 2115-2117. In the illustrated example of FIG. 21, the example reader badges 2105, 2106 are carried by respective caregivers as they move through the environment 2100. In addition, the example reader badges 2105, 2106 of FIG. 21 are associated with respective proximity areas 2105a, 2106a. For example, the example first reader badge 2105 may receive beacon messages within the first proximity area 2105a, and the example second reader badge 2106 may receive beacon messages within the second proximity area 2106a. The example fixed-location asset beacon tags 2110-2114 are affixed to different portions of an example hall 2101 of the environment 2100. The example first mobile-location asset beacon tag 2115 is affixed to a first piece of equipment (e.g., a wheelchair), the example second mobile-location asset beacon tag 2116 is affixed to a second piece of equipment (e.g., a cot), and the example third mobile-location asset beacon tag 2117 is affixed to a patient (e.g., affixed to a patient ID band).

In the illustrated example of FIG. 21, the example first proximity area 2105a overlaps with the first fixed-location asset beacon tag 2110 and does not overlap with the other fixed-location asset beacon tags 2110-2114. Thus, the first fixed-location asset beacon tag 2110 may be determined to be the nearest fixed-location asset beacon tag to the reader badge 2105. In addition, the location of the fixed-location asset beacon tag 2110 may be mapped to the reader badge 2105.

Once the reader badge-location mapping for the first reader badge 2105 is determined, the location(s) for relatively-near and/or relatively-immediate mobile-location assets may be determined. In the illustrated example of FIG. 21, the first proximity area 2105a overlaps with the first mobile-location asset beacon tag 2115 and, thus, the first mobile-location asset may be classified as relatively-immediate to the example first reader badge 2105. In the illustrated example, the location of the first mobile location asset may be updated to the location of the reader badge 2105 (e.g., the location of the fixed-location asset beacon tag 2110). Subsequent beacon messages broadcast by the beacon tag 2115 may then be used to increase the confidence that the corresponding asset is still located proximate to the fixed-location asset beacon tag 2110. For example, each time a caregiver is determined to be located near the fixed-location asset beacon tag 2110 and the beacon tag 2115 is determined to be relatively-near and/or relatively-immediate at that time, confidence of the asset location increases.

In the illustrated example of FIG. 21, the example second proximity area 2106a does not overlap with any of the fixed-location asset beacon tags 2110-2114. In the illustrated example, the nearest fixed-location asset beacon tag may be determined based on signal strength. For example, if the second reader badge 2106 received beacon messages from the second fixed-location asset beacon tag 2111 and the third fixed-location asset beacon tag 2112, the example RTLS server 455 may determine which of the respective beacon messages was associated with a stronger signal strength and assign the location of the corresponding beacon tag as the location of the second reader badge 2106.

Once the reader badge-location mapping for the second reader badge 2106 is determined, the location(s) for relatively near and/or relatively-immediate mobile-location assets may be determined. For example, the second and third example mobile-location asset beacon tags 2116 and 2117, respectively, overlap with the second proximity area 2106. In some such examples, the location of the second and third mobile location assets may be updated to the location of the second reader badge 2106.

In addition, analysis of different timestamp intervals (e.g., timestamp intervals prior to the current timestamp interval and/or timestamp intervals after the current timestamp interval) may enable tracking the movement of the equipment 2116 and the patient 2117. For example, as the second caregiver moves through the environment 2100, the location of the reader badge 2106 also changes. In such instances, while the equipment 2116 and the patient 2117 are classified as relatively-immediate to the second caregiver, the locations of the assets 2116, 2117 are also updated to the changing locations of the reader badge 2106.

As described above, in some examples, the example proximity detection and location tracking system may include one or more dock modules (e.g., the example dock module 700 of FIG. 7) in the environment. In the illustrated example of FIG. 22, an example dock module 2205 is positioned in an example reception area 2200. The example dock module 2205 is associated with an example proximity area 2205a. In the illustrated example, example mobile-location assets are located relatively-immediate to the dock module 2205. For example, example beacon tags 2210-2213 affixed to mobile-location assets (e.g., laptops, forms, chairs, etc.) overlap with the proximity area 2205. In some such examples, the location of the corresponding mobile-location assets may be updated to the location of the dock module 2205 (e.g., the example reception area 2200).

Figure 22:
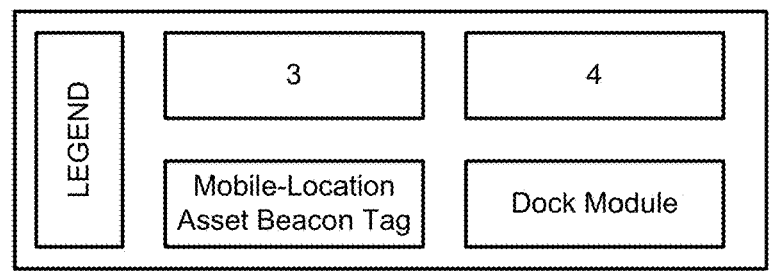
FIG. 22 illustrates another example environment to facilitate proximity detection and location tracking, according to the present disclosure.
Figure 22:
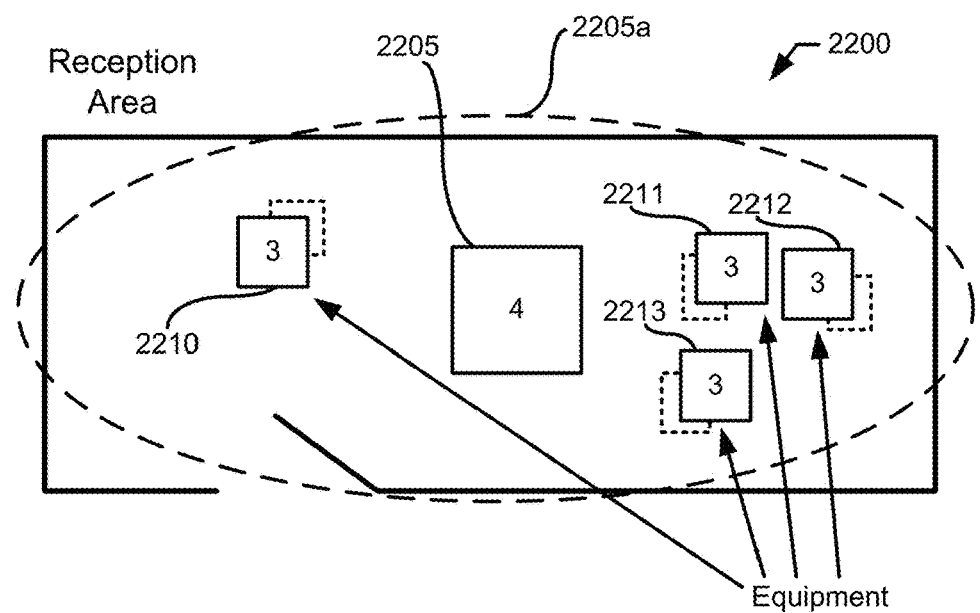

Analysis of the current timestamp interval illustrated in FIG. 22 and analysis of different timestamp intervals may further increase the confidence that the assets are in the reception area 2200. For example, in the illustrated example of FIG. 22, each time a caregiver walks into the reception area 2200 (e.g., is relatively-immediate to the assets 2210-2213), and/or walks near the reception area 2200 (e.g., is relatively-near the assets 2210-2213), confidence scores for the corresponding asset locations increase, and confidence that the corresponding assets are located in the reception area 2200 also increases.

Figure 23:
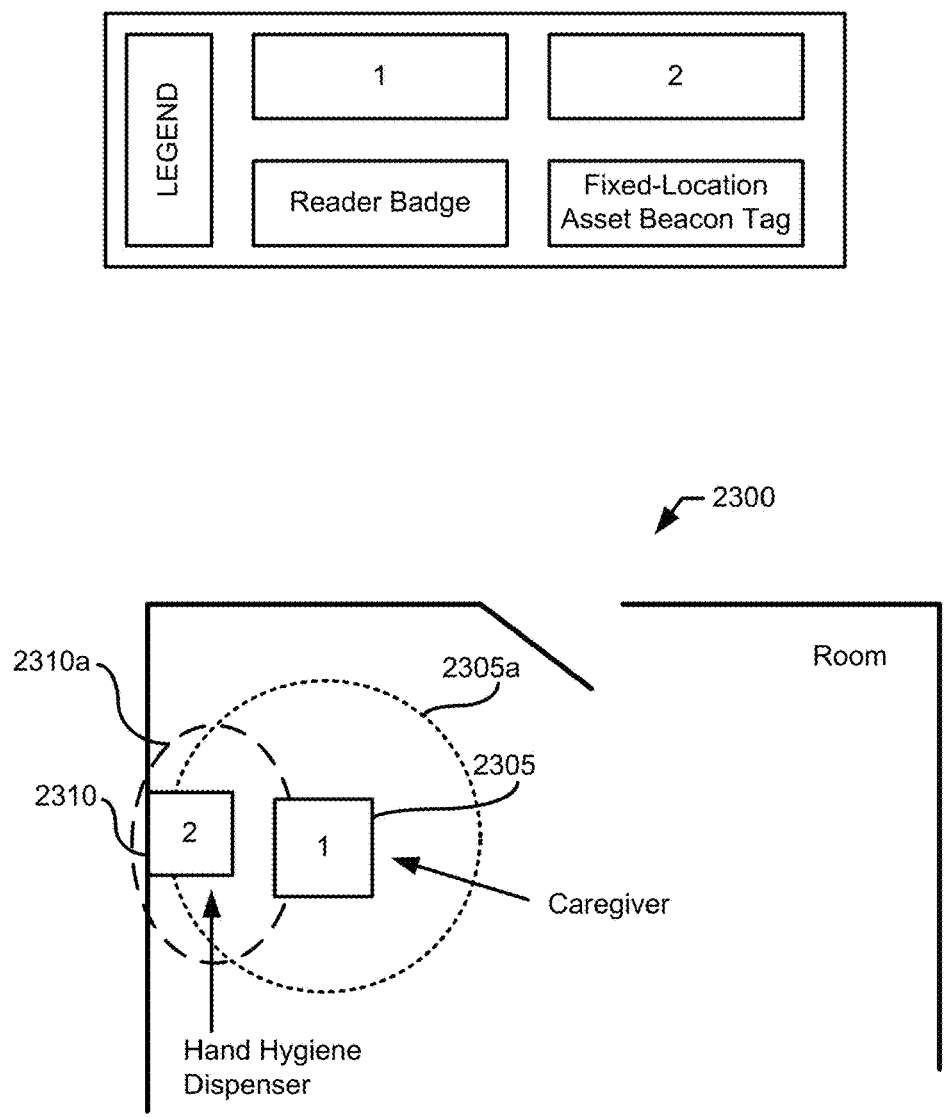
FIG. 23 illustrates another example environment to facilitate proximity detection and location tracking, according to the present disclosure.

FIG. 23 illustrates an example environment 2300 (e.g., a patient room) including an example reader badge 2305 associated with an example proximity area 2305a and an example beacon tag 2310 affixed to a fixed-location asset (e.g., a hand hygiene dispenser). In the illustrated example, the beacon tag 2310 is associated with a broadcast area 2310a. As discussed above, in some examples, user behavior may be determined based on detected proximity. For example, when the proximity area 2305a overlaps with the beacon tag 2310, an interaction between the corresponding caregiver and the fixed-location asset may be determined. In some examples, a dispense event may be detected based on, for example, additional sensor(s) included in the reader badge 2305 and/or by tracking how long the proximity area 2305a and the beacon tag 2310 overlap.

Additionally, based on analysis of the location of the caregiver during different timestamp intervals, a determination may be made whether, for example, the caregiver interacted with the hand hygiene dispenser prior to interacting with a patient in the environment 2300, in the middle of interacting with a patient in the environment 2300 and/or after interacting with a patient in the environment 2300.

Figure 24:
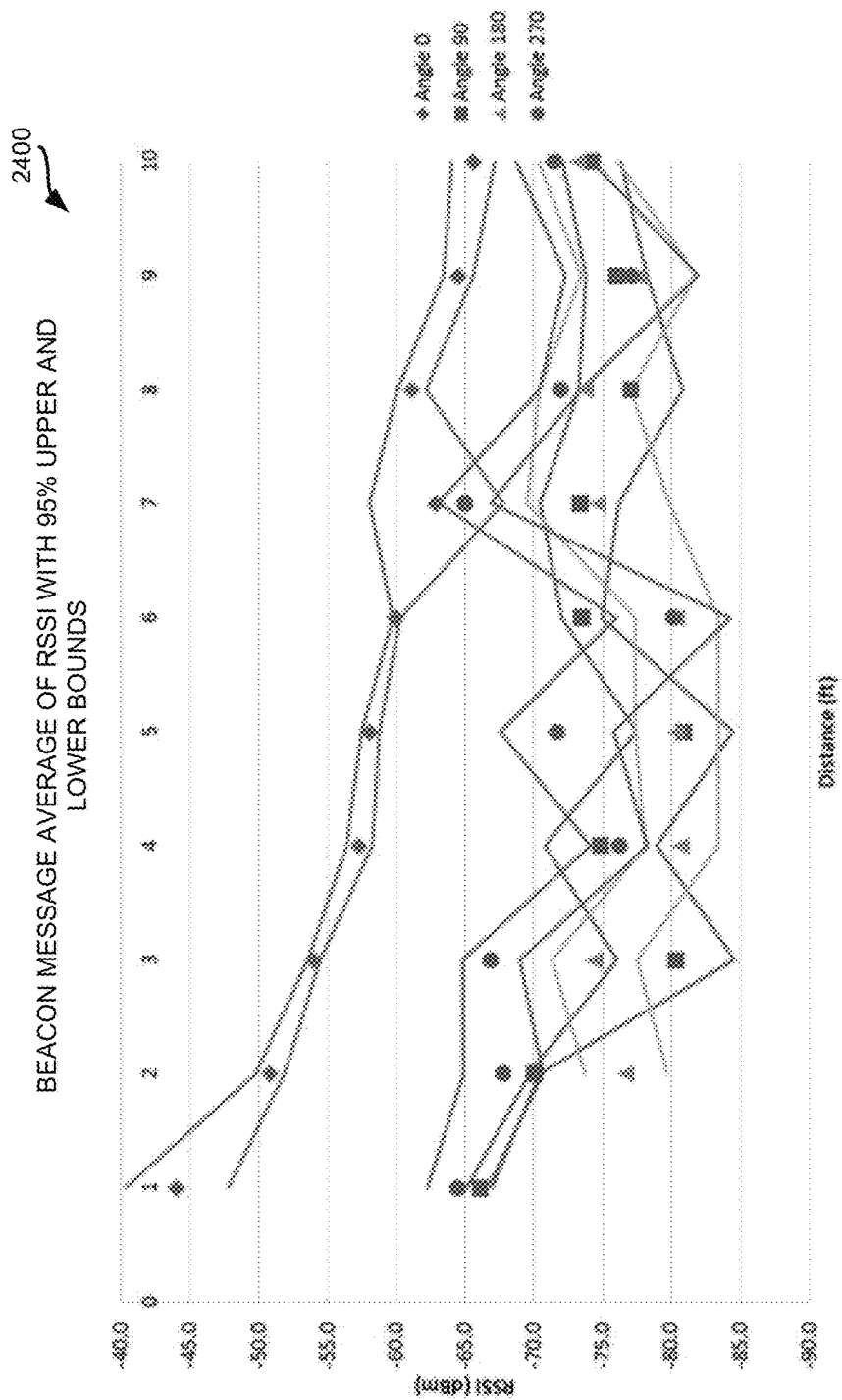
FIG. 24 is an example graph correlating signal strength with distance at different angles of orientation, according the present disclosure.

FIG. 24 is an example graph 2400 correlating average RSSI strength with distance based on the angle at which the example reader badge 425 receives a beacon message 410. In the illustrated example, the graph 2400 also displays the 95% upper and lower bounds of the RSSI strengths measured at different distances.

In the illustrated example of FIG. 24, the signal strength of a beacon message collected by a reader badge corresponds to the distance between the broadcasting beacon tag and the reader badge, and the direction of the reader badge relative to the broadcasting beacon tag. For example, the average RSSI value of a beacon message that is collected by a reader badge located three feet away from the broadcasting beacon tag and positioned so as to directly face the beacon tag (e.g., at a zero degree angle) is approximately (−54) decibels. In contrast, while facing directly away from the beacon tag (e.g., at a 180-degree angle) and at the same distance (e.g., three feet away), the average RSSI value of a beacon message is (−75) decibels.

In some examples, a graph similar to the example graph 2400 of FIG. 24 may be used to determine signal strength thresholds that corresponds to "immediate," "near" and/or "far" distances relative to the collecting reader badge. For example, based on the illustrated example of FIG. 24, beacon messages associated with an RSSI value greater than or equal to (−55) decibels may be classified as "immediate" relative to a reader badge, and beacon messages associated with an RSSI value less than or equal to (−80) decibels may be classified as "far" relative to the reader badge.

Figure 25:
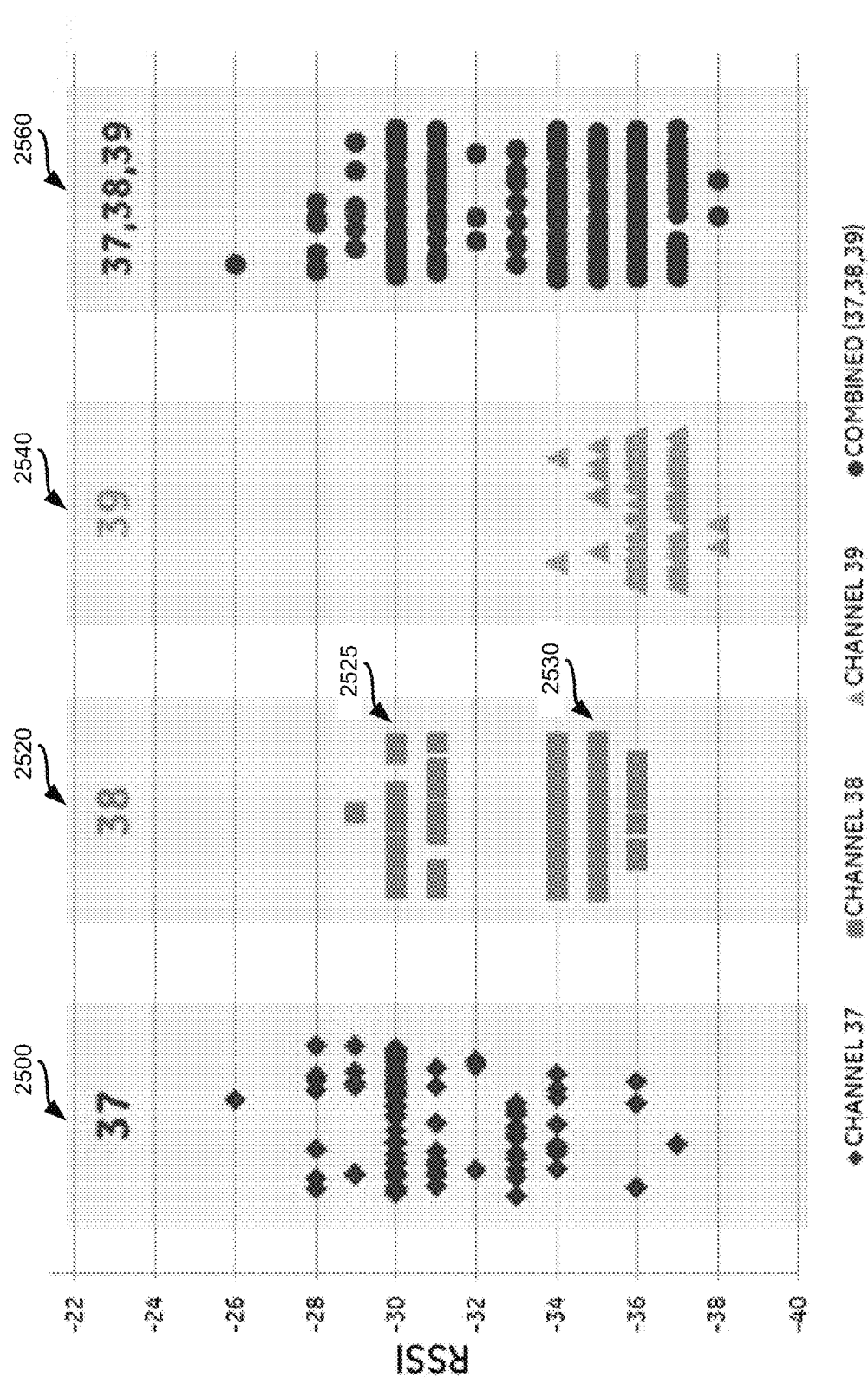
FIG. 25 illustrates signal strength of beacon messages received at a reader badge, according to the present disclosure.

FIG. 25 illustrates signal strength of beacon messages received at the example reader badge 425 at three different channels (e.g., Bluetooth channels 37, 38 and 39). In the illustrated example, looking at the individual channels (e.g., channel 37 versus channel 38 versus channel 39) provides insight on signal strength noise that may be not determined when looking at the channels combined. For example, example graphs 2500, 2520, 2540, 2560 illustrate beacon messages broadcast by a same beacon tag 405 and that are received by a reader badge 425 at a fixed-location three feet away from the beacon tag 405. For example, the example graph 2500 indicates that the beacon tag 405 broadcasts beacon messages via channel 37 with a high variance (e.g., approximately a ten decibel range).

The example graph 2520 indicates two example bands 2525, 2530. The example first band 2525 indicates a portion of beacon messages broadcast via channel 38 were received by the reader badge 425 with an RSSI value of approximately (−30). The example second band 2530 indicates a portion of the beacon messages broadcast via channel 38 were received by the reader badge 425 with an RSSI value of approximately (−36). In the illustrated example, the two distinct bands 2525, 2530 may indicate a first response event and a bounce event. For example, because the signal strength associated with the first band 2525 (e.g., approximately (−30)) is stronger than the signal strength associated with the second band 2530 (e.g., approximately (−36)), the beacon messages received near the first band may be indicative of beacon messages that were received by the reader badge 425 directly from the beacon tag 405 (e.g., without interference). In contrast, the beacon messages received near the second band may be indicative of beacon messages that were received by the reader badge 425 indirectly from the beacon tag 405. For example, the second band beacon messages may be collected by the reader badge 425 after bouncing off a wall.

The example graph 2530 indicates that beacon messages that were broadcast by the beacon tag 405 via channel 39 had a low variance and are associated with an RSSI value of approximately (−36). For example, graph 2530 illustrates a "tight" grouping of RSSI data for channel 39.

The example graph 2560 illustrates the combined beacon messages broadcast via channels 37, 38 and 39. In the illustrated example, the insights gained by viewing the channels separately (e.g., a signal strength range of 10 decibels for beacon messages broadcast via channel 37, two bands of beacon messages broadcast via channel 38, and an approximate signal strength of beacon messages broadcast via channel 39) cannot be determined by analyzing the combined graph 2560. For example, knowing the channel used to broadcast the beacon message may improve the reliability of the data collected.

From the foregoing, it will appreciate that the above disclosed methods, apparatus and articles of manufacture facilitate proximity detection and location tracking of assets in an industrial setting. As described above, example disclosures uniquely eliminate the expensive and difficult-to-maintain infrastructure. An example benefit of the disclosed techniques includes determining location awareness of assets in the industrial setting without constructing a new infrastructure. In some disclosed examples, the location awareness of assets is determined by "crowd-sourcing" probability proximity locations of the assets. Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method to facilitate proximity detection and location tracking in an environment, the method comprising:

initiating, at a badge including a processor, a batch timer;

storing one or more reader messages in a memory at the badge, each reader message tagged with a mobile-location type identifier or a fixed-location type identifier to enable identification of mobile-asset reader messages and aggregation by a location server;

comparing, using the processor, a value of the batch timer to a batch threshold;

when the value satisfies the batch threshold, initiating a connection between the badge and a location server;

transmitting the one or more reader messages from the badge to the location server via the connection; and resetting the batch timer, wherein, when the mobile-location type identifier is associated with a reader message, the mobile-location type identifier is to be used with signal strength information to enable the location server to analyze the one or more reader messages to classify a location of an asset relative to the badge.

2. The method of claim 1, wherein the one or more reader messages include one or more beacon messages received by the badge.

3. The method of claim 2, wherein the one or more beacon messages are associated with location information.

4. The method of claim 2, further including forming the one or more reader messages by combining with badge information with the one or more beacon messages.

5. The method of claim 4, wherein the badge information includes at least one of a) badge identifying information, b) timestamp information, c) signal strength information, or d) channel identifying information.

6. The method of claim 1, wherein the batch threshold provides a periodic transmission interval for the badge based on the batch timer.

7. The method of claim 1, wherein the transmitting the one or more reader messages from the badge to the location server via the connection further includes transmitting the one or more reader messages from the badge to the location server using web service calls via the connection.

8. An apparatus to facilitate proximity detection and location tracking in an environment, the apparatus comprising:

a badge including:

a receiver;

a memory;

a transmitter; and a processor, the processor adapted to:

initiate a batch timer;

store one or more reader messages in the memory, each reader message tagged with a mobile-location type identifier or a fixed-location type identifier to enable identification of mobile-asset reader messages and aggregation by a location server;

compare a value of the batch timer to a batch threshold;

when the value satisfies the batch threshold, initiate a connection between the badge and a location server;

transmit the one or more reader messages from the badge to the location server via the connection; and reset the batch timer, wherein, when the mobile-location type identifier is associated with a reader message, the mobile-location type identifier is to be used with signal strength information to enable the location server to analyze the one or more reader messages to classify a location of an asset relative to the badge.

9. The apparatus of claim 8, wherein the one or more reader messages include one or more beacon messages received by the badge.

10. The apparatus of claim 9, wherein the one or more beacon messages are associated with location information.

11. The apparatus of claim 9, wherein the processor is to form the one or more reader messages by combining with badge information with the one or more beacon messages.

12. The apparatus of claim 11, wherein the badge information includes at least one of a) badge identifying information, b) timestamp information, c) signal strength information, or d) channel identifying information.

13. The apparatus of claim 8, wherein the batch threshold provides a periodic transmission interval for the badge based on the batch timer.

14. The apparatus of claim 8, wherein the processor is to transmit the one or more reader messages from the badge to the location server via the connection by transmitting the one or more reader messages from the badge to the location server using web service calls via the connection.

15. A tangible machine-readable storage medium comprising instructions that, when executed, cause a machine to at least:

initiate a batch timer;

store one or more reader messages in the memory, each reader message tagged with a mobile-location type identifier or a fixed-location type identifier to enable identification of mobile-asset reader messages and aggregation by a location server;

compare a value of the batch timer to a batch threshold;

when the value satisfies the batch threshold, initiate a connection between the badge and a location server;

transmit the one or more reader messages from the badge to the location server via the connection; and reset the batch timer, wherein, when the mobile-location type identifier is associated with a reader message, the mobile-location type identifier is to be used with signal strength information to enable the location server to analyze the one or more reader messages to classify a location of an asset relative to the badge.

16. The storage medium of claim 15, wherein the one or more reader messages include one or more beacon messages received by the badge.

17. The storage medium of claim 16, wherein the one or more beacon messages are associated with location information.

18. The storage medium of claim 16, wherein the instructions cause the machine to form the one or more reader messages by combining with badge information with the one or more beacon messages.

19. The storage medium of claim 18, wherein the badge information includes at least one of a) badge identifying information, b) timestamp information, c) signal strength information, or d) channel identifying information.

20. The storage medium of claim 15, wherein the batch threshold provides a periodic transmission interval for the badge based on the batch timer.

* * * * *